United States Patent [19]
Kleinschroth et al.

[11] Patent Number: 5,945,440
[45] Date of Patent: Aug. 31, 1999

[54] INDOLOCARBAZOLE IMIDES AND THE USE THEREOF

[75] Inventors: Jürgen Kleinschroth, Denzlingen; Christoph Schächtele, Freiburg; Johannes Hartenstein, Stegen-Wittental; Claus Rudolph, Vörstetten; Hubert Barth, Emmendingen; Julian Aranda; Hans Jürgen Betche, both of Vörstetten, all of Germany

[73] Assignee: Goedecke Aktiengesellschaft, Berlin, Germany

[21] Appl. No.: 09/074,139

[22] Filed: May 7, 1998

Related U.S. Application Data

[62] Division of application No. 08/343,435, filed as application No. PCT/EP93/01347, May 28, 1993, Pat. No. 5,883,114.

[30] Foreign Application Priority Data

May 30, 1992 [DE] Germany ............... 42 17 964

[51] Int. Cl.⁶ ................................ A61K 31/40
[52] U.S. Cl. ........................................ 514/410
[58] Field of Search ............................ 514/410

[56] References Cited

U.S. PATENT DOCUMENTS

| | | | |
|---|---|---|---|
| 5,106,864 | 4/1992 | Suda et al. | 514/410 |
| 5,217,885 | 6/1993 | Suda et al. | 435/119 |
| 5,547,976 | 8/1996 | Slater et al. | 514/410 |

FOREIGN PATENT DOCUMENTS

| | | |
|---|---|---|
| 0388956 | 9/1990 | European Pat. Off. . |
| 0528030 | 2/1993 | European Pat. Off. . |

OTHER PUBLICATIONS

Bergman and Pelcman, "Synthesis of Indolo[2,3–a]pyrrolo[3,4–c]carbazoles by Double Fischer Indolizations", *J. Org. Chem.*, vol. 54, 1989, 824–828.

Toullec et al., "The Bisindolylmaleimide GF 109203X Is a Potent and Selective Inhibitor of Protein Kinase C", *J. Biol. Chem.*, vol. 266, No. 24, 1991, 15771–15781.

Kaneko and Wong, "Two Synthetic Approaches to Rebeccamycin", *Tetrahedron Letters*, vol. 26, No. 34, 1985, 4015–4018.

Bergman and Pelcman, "Coupling of indoleacetic acid trianion or methyl indoleacetic acid dianion. A biomimetic approach to indolocarbazole alkaloids", *Tetrahedron Letters*, vol. 28, No. 38, 1987, 4441–4444.

Tanaka et al., "A new indolopyrrolocarbazole antitumor substance, ED–110, a derivative of BE–13793C", *J. Antibiotics*, vol. 45, No. 11, 1992, 1797–1798.

*Primary Examiner*—Laura L. Stockton
*Attorney, Agent, or Firm*—Elizabeth M. Anderson

[57] ABSTRACT

The present invention is concerned with the use of indolocarbazole imides of the general formula (I):

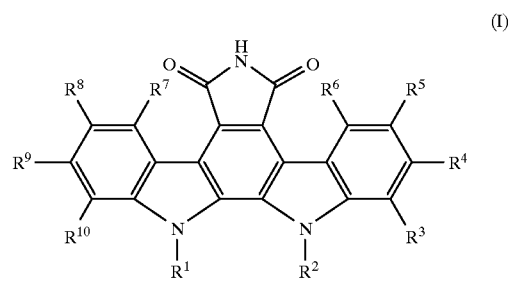

for the preparation of pharmaceutical compositions for the treatment and/or prevention of cancer, virus diseases (for example HIV infections), heart and blood vessel diseases (for example high blood pressure, thromboses, heart rhythm disturbances and atheroscleroses), bronchopulmonary diseases, degenerative diseases of the central nervous system (for example Alzheimer's disease), inflammatoryl diseases (for example rheumatism and arthritis), diseases of the immune system (for example allergies), as well as psoriasis and for use as immune suppressives; as well as new compounds of general formula (I).

30 Claims, No Drawings

INDOLOCARBAZOLE IMIDES AND THE USE THEREOF

CROSS REFERENCE TO RELATED APPLICATION

This application is a divisional of U.S. Ser. No. 08/343,435, filed Feb. 15, 1995, now U.S. Pat. No. 5,883,114 incorporated herein by reference, and filed as PCT/EP93/01347, May 28, 1993.

The present invention is concerned with the use of indolocarbazole imides, some of which are new, for the preparation of pharmaceutical compositions for the treatment and/or prevention of cancer, virus diseases, heart and blood vessel diseases, bronchopulmonary diseases, degenerative diseases of the central nervous system, inflammatory diseases, diseases of the immune system and psoriasis and for use as immune suppressives.

More particularly, the present invention is concerned with the use of indolocarbazole imides of the general formula (I):

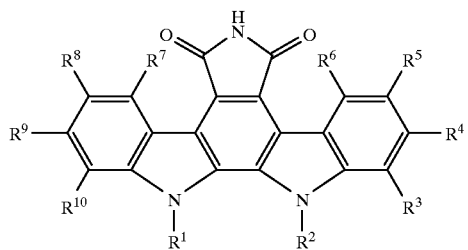

(I)

wherein $R^1$ and $R^2$ are the same or different and are in each case, a hydrogen atom, a straight-chained or branched alkyl, alkenyl or alkynyl radical containing up to 6 carbon atoms, an epoxyalkyl radical containing up to 4 carbon atoms, an unsubstituted or substituted aryl or aralkyl radical containing, in each case, up to 12 carbon atoms, a cyano group, a straight-chained or branched cyanoalkyl, cyanoalkenyl, cyanoalkynyl, dicyanoalkyl, dicyanoalkenyl, azidoalkyl, azidoalkenyl, haloalkyl, di- or trihaloalkyl, halohydroxyalkyl, hydroxyalkyl, acyloxyalkyl, dihydroxyalkyl, alkoxyalkyl, alkylthioalkyl, alkylsulphinylalkyl, alkylsulphonylalkyl, cyanoalkoxyalkyl, cyanoalkylthioalkyl, isocyanoalkyl, carboxyalkyl, amidinoalkyl, amidinothioalkyl, (2-nitroguanidino)-alkyl, cyanatoalkyl, isocyanatoalkyl, thiocyanatoalkyl or isothiocyanatoalkyl radical, in each case containing up to 6 carbon atoms, an arylsulphonyloxyalkyl or alkylsulphonyloxyalkyl radical containing up to 12 carbon atoms, a straight-chained or branched aminoalkyl group containing up to 12 carbon atoms unsubstituted on the nitrogen atom or mono-, di- or trisubstituted by benzyl radicals or alkyl radicals containing up to 4 carbon atoms or in which two substituents on the nitrogen atom, together with the nitrogen atom or a substituent on the nitrogen atom and a substituent of the alkyl chain and together with the nitrogen atom form a heterocyclic ring containing 3 to 6 carbon atoms which can also contain oxygen, sulphur and/or further nitrogen atoms and can be substituted by alkyl radicals containing up to 4 carbon atoms, whereby the alkyl chain can be substituted by further $C_1$–$C_4$-alkyl radicals, a hydroxyl group or a $C_1$–$C_4$-alkoxy radical, an acylaminoalkyl radical containing up to 6 carbon atoms, an alkoxycarbonylalkyl radical containing up to 7 carbon atoms, a radical of the general formula:

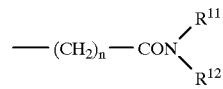

in which n is 1, 2 or 3 and $R^{11}$ and $R^{12}$ can be the same or different and, in each case, are a hydrogen atom or an alkyl radical containing up to 6 carbon atoms or an acyl radical containing up to 4 carbon atoms or $R^1$ and $R^2$ together signify an alkylene radical containing 2 to 4 carbon atoms which is optionally substituted by a hydroxy group, an alkoxy radical containing up to 4 carbon atoms or an amino group which is unsubstituted or can be mono- or disubstituted by benzyl radicals or alkyl radicals containing up to 4 carbon atoms and $R^3$ to $R^{10}$, independently of one another, are each a hydrogen atom, a $C_1$–$C_4$-alkyl, $C_1$–$C_4$-alkoxy, $C_1$–$C_4$-alkylthio, benzyloxy, $C_1$–$C_4$-acyl, halogen, nitro, hydroxyl, acyloxy, trifluoromethyl, amino, unsubstituted or mono- or disubstituted by benzyl radicals or alkyl radicals containing up to 4 carbon atoms, aminoalkyl or aminoalkoxy containing up to 12 carbon atoms, unsubstituted on the nitrogen atom or mono- or di-substituted by benzyl radicals or alkyl radicals containing up to 4 carbon atoms, hydroxyalkyl containing up to 4 carbon atoms, carboxyl, acylamino containing up to 4 carbon atoms, haloalkyl containing up to 4 carbon atoms, $C_1$–$C_4$-alkylsulphinyl or alkylsulphonyl, sulpho, carbamoyl, mono- or di-($C_1$–$C_4$-alkyl)-carbamoyl or cyano or two neighbouring radicals together stand for a methylenedioxy radical, with the proviso that if $R^3$ and $R^{10}$ simultaneously stand for hydroxyl groups, all of the other symbols $R^1$ to $R^{11}$ cannot stand for hydrogen atoms, as well as of the pharmacologically acceptable salts thereof for the preparation of pharmaceutical compositions for the treatment and/or prevention of cancer, virus diseases (for example HIV infections), heart and blood vessel diseases (for example high blood pressure, thromboses, heart rhythm disturbances and atheroscleroses), bronchopulmonary diseases, degenerative diseases of the central nervous system (for example Alzheimer's disease), inflammatory diseases (for example rheumatism and arthritis), diseases of the immune system (for example allergies), as well as psoriasis and for use as immune suppressives.

Compounds of general formula I are preferred in which $R^1$ and $R^2$ are the same or different and, in each case, are a hydrogen atom, a straight-chained or branched $C_1$–$C_4$-alkyl or $C_3$–$C_6$-alkenyl radical, a straight-chained or branched cyanoalkyl, cyanoalkenyl, azidoalkyl, azidoalkenyl, chloroalkyl, bromoalkyl, fluoroalkyl, chlorohydroxyalkyl, hydroxyalkyl, acetoxyalkyl, dihydroxyalkyl, alkoxyalkyl, alkylthioalkyl, cyanoalkoxyalkyl, isocyanoalkyl, carboxalkyl, amidinoalkyl, amidinothioalkyl or (2-nitroguanidino)-alkyl radical containing, in each case, up to 6 carbon atoms, a straight-chained or branched aminoalkyl radical containing up to 12 carbon atoms, unsubstituted on the nitrogen atom or mono-, di- or trisubstituted by alkyl radicals containing up to 4 carbon atoms or in the case of which two substituents on the nitrogen atom together with the nitrogen atom or a substituent on the nitrogen atom and a substituent of the alkyl chain and together with the nitrogen atom form a heterocyclic ring containing 3 to 6 carbon atoms which can also contain oxygen, sulphur and/or further nitrogen atoms and can be substituted by alkyl radicals containing up to 4 carbon atoms, whereby the alkyl chain can be substituted by further $C_1$–$C_4$-alkyl radicals, a hydroxyl group or a $C_1$–$C_4$-alkoxy radical, an alkoxycarbonylalkyl radical containing up to 6 carbon atoms, a radical of the general formula:

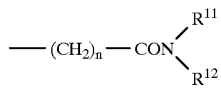

in which n is 1, 2 or 3 and $R^{11}$ and $R^{12}$ are the same or different and, in each case, stand for a hydrogen atom or an alkyl radical containing up to 6 carbon atoms or $R^1$ and $R^2$ together signify an alkylene radical containing 2 to 4 carbon atoms which can optionally be substituted by a hydroxyl group, and $R^3$ to $R^{10}$ have the above-given meanings.

Especially preferred are compounds of the general formula I in which $R^1$ and $R^2$ are the same or different and are, in each case, a hydrogen atom or a straight-chained or branched $C_1$–$C_4$-alkyl radical, a straight-chained or branched cyanoalkyl, azidoalkyl, hydroxyalkyl, dihydroxyalkyl, chlorohydroxyalkyl, cyanoalkoxyalkyl, isocyanoalkyl, amidinoalkyl or amidinothioalkyl radical containing, in each case, up to 6 carbon atoms, an unsubstituted or substituted aminoalkyl radical containing up to 12 carbon atoms, such as an unsubstituted aminoalkyl radical, especially 2-aminoethyl, 3-aminopropyl, 4-aminobutyl, 5-aminopentyl or 1-amino-2-propyl radical, an N,N-dialkylaminoalkyl or N,N-alkylbenzylaminoalkyl radical containing $C_1$–$C_4$-alkyl substituents on the nitrogen atoms and containing up to 4 carbon atoms in the alkyl chain, whereby the alkyl chain can be substituted by further $C_1$–$C_4$-alkyl radicals, a hydroxyl group or a $C_1$–$C_4$-alkoxy radical, especially 2-dimethylaminoethyl, 3-dimethylamino-1-propyl, 3-dimethylamino-2-propyl, 3-diethylamino-1-propyl, 3-methylamino-1-propyl, 3-isopropylamino-1-propyl, 3-diisopropylamino-1-propyl, 3-ethylamino-1-propyl, 2-diethylaminoethyl, 2-(N-benzyl-N-methylamino)-ethyl, 3-(N-benzyl-N-methylamino)-propyl, 3-diethylamino-2-hydroxy-1-propyl, 3-diethylamino-2-methoxy-1-propyl, 3 -methylamino-2-hydroxy-1-propyl, 3-ethylamino-2-hydroxy-1-propyl, 3-isopropylamino-2-hydroxy-1-propyl, 3-diisopropylamino-2-hydroxy-1-propyl, 4-dimethylamino-3-hydroxy-1-butyl, 3-dimethylamino-2-methoxy-1-propyl, 3-dimethylamino-2-hydroxy-1-propyl, 2-piperidinoethyl, 3-piperidinopropyl, 2-pyrrolidinoethyl, 3-pyrrolidino-propyl, 3-pyrrolidino-2-hydroxy-1-propyl, 2-morpholino-ethyl, 3-morpholinopropyl, 3-morpholino-2-hydroxy-1-propyl, pyrrolidin-2-ylmethyl or N-methylpyrrolidin-2-ylmethyl radical, a radical of the general formula:

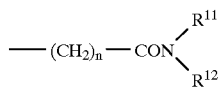

in which n is 1, 2 or 3 and $R^{11}$ and $R^{12}$ are the same or different and, in each case, are a hydrogen atom or an alkyl radical containing up to 4 carbon atoms, or $R^1$ and $R^2$ together signify an alkylene radical containing 2 to 4 carbon atoms which can optionally be substituted by a hydroxyl group and $R^3$ and $R^{10}$, independently of one another, each stand for a hydrogen atom, $C_1$–$C_4$-alkyl, $C_1$–$C_4$-alkoxy, benzyloxy, formyl, acetyl, propionyl, chlorine, bromine, nitro, hydroxyl, acetoxy, trifluoromethyl, amino, methylamino, dimethylamino, aminomethyl, aminoethyl, dimethylaminomethyl, dimethylaminoethyl, 3-dimethylaminopropoxy, hydroxymethyl, hydroxyethyl, acetamido, dimethyl- or diethylcarbamoyl, or cyano or two neighbouring radicals together stand for a methylenedioxy radical.

Quite especially preferred are compounds of general formula I in which $R^1$ and $R^2$ are the same or different and, in each case, are a hydrogen atom or a methyl, ethyl, cyanomethyl, 2-cyanoethyl, 3-cyanopropyl, 3-cyano-2-propyl, 2-azidoethyl, 3-azidopropyl, 2,3-dihydroxypropyl, 3-chloro-2-hydroxy-1-propyl, 3-amino-propyl, 3-dimethylaminopropyl, 3-trimethylammoniopropyl, 4-aminobutyl, 5-aminopentyl, epoxymethyl, 3-methylaminopropyl, 3-ethylaminopropyl, 3-isopropylaminopropyl, 3-diisopropylaminopropyl, 3-methylamino-2-hydroxy-1-propyl, 3-ethylamino-2-hydroxy-1-propyl, 3-isopropylamino-2-hydroxy-1-propyl, 3-dimethylamino-2-hydroxy-1-propyl, 3-diethylamino-2-hydroxy-1 -propyl, 3-diisopropylamino-2-hydroxy-1-propyl, 3-pyrrolidino-2-hydroxy-1-propyl or the radical —$(CH_2)_2CONH_2$ and $R^3$ to $R^{10}$, independently of one another, each stand for hydrogen, methyl, methoxy, n-propoxy, chlorine, bromine, nitro, hydroxyl or amino or two neighbouring radicals together stand for a methylenedioxy radical, in each case with the proviso that if $R^3$ and $R^{10}$ simultaneously stand for hydroxyl groups, not all of the symbols $R^1$ to $R^{10}$ stand for hydrogen atoms.

Especially preferred are compounds of general formula I in which $R^1$ and $R^2$ have the above-given meanings but at least one of the radicals $R^1$ and $R^2$ is other than a hydrogen atom and $R^3$ to $R_{10}$ have the above-given meanings.

Compounds of general formula I which have a chiral centre in the radicals $R^1$ to $R^{10}$ can be used as stereoisomeric mixtures or in the form of the enantiomers. The enantiomers can be obtained by means of the processes normally employed for the optical separation of stereoisomers.

Basic compounds of general formula I which have a basic centre on at least one of the radicals $R^1$ to $R^{10}$ are, for the purpose of purification and for galenical reasons, preferably converted into crystalline, pharmacologically acceptable salts. The salts are obtained in the usual manner by neutralisation of the bases with appropriate inorganic or organic acids. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid. The acid addition salts are, as a rule, obtained in known manner by mixing the free base or a solution thereof with the appropriate acid or a solution thereof in an organic solvent, for example a lower alcohol, such as methanol, ethanol or propan-2-ol, or a lower ketone, such as acetone or butan-2-one, or an ether, such as diethyl ether, diisopropyl ether, tetrahydrofuran or dioxane.

The compounds can be administered enterally or parenterally in the particularly appropriate formulation in doses of from 1 to 500 mg/kg and preferably of from 1 to 50 mg/kg.

The compounds of general formula I according to the present invention can be administered orally or parenterally in liquid or solid form. As injection medium, water is preferably used which contains the additives usual in the case of injection solutions, such as stabilising agents, solubilising agents and/or buffers.

Additives of this kind include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain additional flavouring and/or sweetening materials.

The present invention also provides new indolecarbazoles of general formula I in which the substituents have the above-given meanings but with the proviso that 1. not all of the symbols simultaneously stand for hydrogen atoms and that
2. all the other symbols cannot simultaneously be hydrogen atoms when (a) $R^1$ is a 3-dimethylaminopropyl radical or when (b) $R^3$ and $R^{10}$ are simultaneously chloride, hydroxyl or methoxy or when (c) $R^4$ and/or $R^9$ are chloride, hydroxyl or methoxy or when (d) $R^5$ and/or $R^8$ are methyl, methoxy, benzyloxy, chloride, bromine or fluorine.

Quite especially preferred are compounds of general formula I in which $R^1$ and $R^2$ are the same or different and, in each case, are hydrogen, methyl, ethyl, cyanomethyl, 2-cyanoethyl, 3-cyanopropyl, 3-cyano-2-propyl, 2-azidoethyl, 3-azidopropyl, 2,3-dihydroxypropyl, 3-chloro-2-hydroxy-1-propyl, 3-aminopropyl, 3-dimethylaminopropyl, 3-trimethylammoniopropyl, 4-aminobutyl, 5-aminopentyl, epoxymethyl, 2-epoxyethyl, 3-methylaminopropyl, 3-ethylaminopropyl, 3-isopropylaminopropyl, 3-diisopropylaminopropyl, 3-methylamino-2-hydroxy-1-propyl, 3-ethylamino-2-hydroxy-1-propyl, 3-isopropyl-amino-2-hydroxy-1-propyl, 3-dimethylamino-2-hydroxy-1-propyl, 3-diethylamino-2-hydroxy-1-propyl, 3-diiso-propylamino-2-hydroxy-1-propyl, 3-pyrrolidino-2-hydroxy-1-propyl or the radical —(CH$_2$)$_2$CONH$_2$ and $R^3$ and $R^{10}$ independently of one another, each stand for hydrogen, methyl, methoxy, n-propoxy, chloride, bromine, nitro, hydroxyl or amino or two neighbouring radicals together stand for a methylenedioxy radical.

Especially preferred are compounds of general formula I in which $R^1$ and $R^2$ have the above-given meanings but at least one of the radicals $R^1$ or $R^2$ is other than a hydrogen atom and $R^3$ to $R^{10}$ have the above-given meanings.

Compounds of general formula I which have a chiral centre in the radicals $R^1$ to $R^{10}$ can be used as stereo-isomers or in the form of enantiomers. The enantiomers can be obtained by means of the processes which are usually employed for the optical separation of stereoisomers.

Depending upon the substitution, compounds of general formula I are potent inhibitors of protein kinase C or of myosine light-chain kinase. Thus, they can be used for the treatment and/or prevention of cancer, virus diseases (for example HIV infections), heart and blood vessel diseases (for example high blood pressure, thromboses, heart rhythm disturbances and atheroscleroses), bronchopulmonary diseases, degenerative diseases of the central nervous system (for example Alzheimer's disease), inflammatory diseases (for example rheumatism and arthritis), diseases of the immune system (for example allergies), as well as psoriasis. Furthermore, the compounds can be used as immune suppressives.

Depending upon the substitution, the preparation of the compounds of general formula I can take place according to one of the processes described hereinafter:

A) By oxidative cyclisation of known bis-indolylmaleimides of the general formula (II):

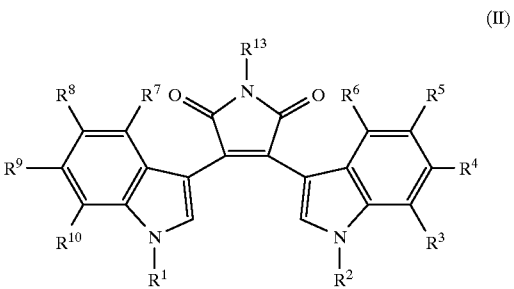

in which $R^1$ to $R^{10}$ possess the above-given meanings and $R^{13}$ is a hydrogen atom, a methyl radical or a protective group Z which can easily be split off (see Tetrahedron, 1988, 44, 2887; Angew. Chem., 1990, 92, 463; EP 0 328 026; Tetrahedron Lett., 1990, 31, 5201; EP 0 397 060; German Patent Application P 39 14 764.9) or of new bis-indolyl-maleimides of the general formula II which have been prepared in a manner analogous to that described in the literature to give compounds of the general formula I or III:

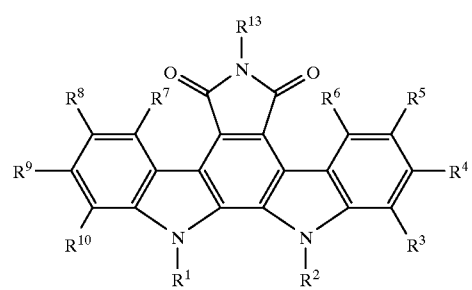

I: $R^{13}$ = H
III: $R^{13}$ = —CH$_3$ or Z

Compounds of general formula III, in which $R^1$ and/or $R^2$ is an unsubstituted, N-mono- or N,N-disubstituted 3-amino-2-hydroxy-1-propyl radical or a 4-amino-3-hydroxy-1-butyl radical, are preferably prepared by the reaction of compounds of general formula III, in which the corresponding radicals $R^1$ and/or $R^2$ stand for an epoxymethyl or 2-epoxyethyl radical, with ammonia or an amine of the general formula HNRR', in which R and R' stand for hydrogen or a C$_1$–C$_4$-alkyl radical or in which R and R', together with the nitrogen atom, form a heterocyclic ring containing 3 to 6 carbon atoms which can also contain oxygen, sulphur and/or further nitrogen atoms and can be substituted by C$_1$–C$_4$-alkyl radicals.

Compounds of general formula III, in which $R^{13}$ is a methyl radical, are converted in an analogous manner to the reaction of compounds of general formula II, in which $R^{13}$ is a methyl radical, into compounds of general formula II in which $R^{13}$ is a hydrogen atom, (see Tetrahedron, 1988, 44, 2887) by reaction with potassium hydroxide in water or an alcohol into the corresponding anhydrides and these are converted in known manner into the corresponding unsubstituted imides of general formula I by reaction with ammonia, ammonium acetate or with hexamethyldisilazane and methanol in dimethylformamide (see Tetrahedron Lett., 1990, 5201).

Compounds of general formula III, in which $R^{13}$ is a protective group, for example a 2-(trimethylsilyl)-ethoxymethyl radical (SEM), are also converted into the corresponding unsubstituted imides of general formula I by appropriate splitting off of the protective group Z (SEM for example with tetrabutylammonium fluoride; see J. Org. Chem., 1984, 49, 203).

The described process of the oxidative cyclisation of bis-indolylmaleimides of general formula II to indolocarbazoles of general formula I is, in principle, not new and has already been used for the synthesis of known indolocarbazoles of general formula I (see Angew. Chem., 1980, 92, 463; Tetrahedron Lett., 1985, 26, 4015; Heterocycles, 1984, 21, 309; J. Org. Chem., 1987, 52, 1117; Tetrahedron, 1981, 28, 4441; EP 0 370 236). For carrying out the cyclisation, it is preferred to heat with a quinone, for example chloranil or 2,3-dichloro-5,6-dicyano-p-benzoquinone (DDQ), and an appropriate acid, preferably p-toluenesulphonic acid, in toluene or chlorobenzene. The other methods described in the literature for this oxidative cyclisation can, in some cases, also be used.

B) By substitution of indolocarbazoles of general formula Ia or IIIa which are either known and prepared by processes known from the literature (see Tetrahedron Lett., 1983, 24, 1441; J. Chem. Soc., 1990, 2475; J. Org. Chem., 1989, 54, 824; St. J. Berthel and G. W. Gribble, 197th ACS National Meeting, Dallas, Tex., U.S.A., 1989, Abstract 116) or of new indolocarbazoles of general formula Ia or IIIa prepared analogously to the processes known from the literature or according to process A:

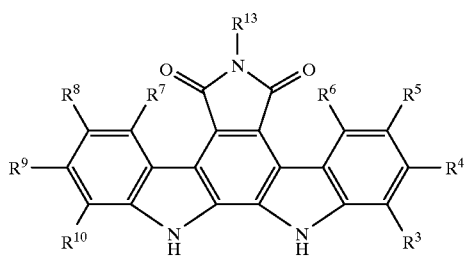

Ia: $R^{13} = H$
IIIa: $R^{13} = CH_3$ or Z in which $R^1$ and $R^2$ are hydrogen atoms, on one or both indole nitrogen atoms, for example by alkylation with a compound of the general formula:

$$R^{14}\text{-}X \qquad (IV)$$

in which $R^{14}$ has one of the meanings given for $R^1$ and $R^2$ and X is an appropriate group which can be split off for example chlorine, bromine, iodine or tosyl, under reaction conditions which are known and appropriate for the alkylation of indoles to carbazoles, to give compounds of general formula I or III. Compounds of general formula I or III mono-substituted on the indole nitrogen atom according to process B, in which one of the symbols $R^1$ or $R^2$ is a hydrogen atom, can be converted by a further substitution according to process B into compounds of general formula I or III disubstituted on the indole nitrogen atom in which $R^1$ and $R^2$ have different meanings.

Compounds of general formula III according to process B are subsequently converted into compounds of general formula I as described in the case of process A.

Compounds of general formula I or III according to process B, in which $R^1$ and/or $R^2$ stands for a 2-cyanoethyl or 3-cyano-2-propyl radical, a 2-alkoxycarbonylethyl radical containing up to 7 carbon atoms or a 2-carbamoylethyl radical, are preferably prepared by the base-catalysed Michael addition of compounds of general formula I or III, in which $R^1$ and/or $R^2$ stand for hydrogen, to activated olefins of the general formula (V):

$$R^{15}\text{-CH}=\text{CH-}R^{16} \qquad (V)$$

in which $R^{15}$ is a hydrogen atom or a methyl radical and $R^{16}$ is a cyano group or $R^{15}$ is a hydrogen atom and $R^{16}$ is an alkoxycarbonyl radical containing up to 5 carbon atoms or is —$CONH_2$. An especially preferred base is 1,8-diazabicyclo[5.4]undec-7-ene (DBU) and, as solvent, it is preferred to use acetonitrile or dimethylformamide.

Compounds of general formula I or III according to process B, in which $R^1$ and/or $R^2$ stands for an N,N-disubstituted 3-amino-2-hydroxy-1-propyl radical, are prepared by the alkylation of compounds of general formula I or III, in which $R^1$ and/or $R^2$ is a hydrogen atom, with 1,1-disubstituted 3-hydroxyazetidinium halides (see J. Org. Chem., 1968, 523).

Compounds of general formula I or III according to process B, in which $R^1$ and $R^2$ together form a substituted propylene radical of the general formula (VI):

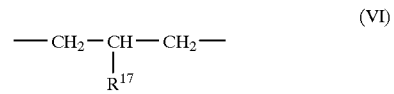

in which $R^{17}$ is a hydroxyl group, an alkoxy radical containing up to 4 carbon atoms or an amino group which is unsubstituted or mono- or disubstituted by a benzyl radical or an alkyl radical containing up to carbon atoms, are prepared by the reaction of compounds of general formula Ia or IIIa, in which $R^1$ and $R^2$ are hydrogen atoms, with two equivalents of a base and epichlorohydrin or epibromohydrin, whereby the initially formed hydroxy-substituted propylene radical can be converted by known methods into $C_1$–$C_4$-alkoxy- or amino-substituted propylene radicals.

Compounds of general formula I or III, in which $R^1$ and $R^2$ together form an alkylene radical containing 2 to 4 carbon atoms, are prepared by the alkylation of compounds of general formula Ia or IIIa, in which $R^1$ and $R^2$ are hydrogen atoms, with two equivalents of a base, for example sodium hydride, and a dihaloalkane, for example, 1,4-dibromobutane or 1,3-dibromopropane.

Compounds of general formula I or III, in which $R^1$ and/or $R^2$ stands for a methyl or ethyl radical, can also be prepared by alkylation with dimethyl or diethyl sulphate in known manner. Compounds of general formula I and III, in which $R^1$ and/or $R^2$ stand for a cyano group, are prepared by the reaction of compounds of general formula I or III, in which $R^1$ and/or $R^2$ stand for a hydrogen atom, with sodium hydride and phenyl cyanate in dimethylformamide analogously to the method described in the literature (see Tetrahedron Lett., 1990, 31, 3681).

In the case of compounds of general formula I or III, in which one or both of the substituents $R^1$ and/or $R^2$ has been introduced by reaction with an alkylation agent of general formula IV according to process B, the introduced radical $R^1$ and/or $R^2$ can subsequently be so modified according to usual methods of organic chemistry (see, for example, Houben-Weyl, Methoden der organischen Chemie, pub. Georg Thieme Verlag, Stuttgart, 1966), for example by hydrolysis, ether cleavage, amide formation or reduction, that they contain other meanings for $R^1$ and $R^2$. Thus, for example, compounds of general formula I or III, in which $R^1$ and/or $R^2$ stand for a carboxyalkyl radical, are preferably prepared by acidic or basic hydrolysis of compounds of general formula I or III, in which $R^1$ and/or $R^2$ stand for an alkoxycarbonylalkyl radical.

Compounds of general formula I or III, in which $R^1$ and/or $R^2$ stand for a hydroxyalkyl radical, can also be prepared by the hydrolysis of compounds of general formula I or III, in which $R^1$ and/or $R^2$ stand for a haloalkyl radical, or by ether cleavage of compounds of general formula I or III, in which $R^1$ and/or $R^2$ stand for an alkoxyalkyl radical, or by the reaction of compounds of general formula I or III, in which $R^1$ and/or $R^2$ stand for hydrogen, with an alkylene oxide, for example propylene oxide.

Compounds of general formula I or III, in which $R^1$ and/or $R^2$ stand for a radical of the general formula:

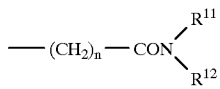

are prepared by the reaction of compounds of general formula I or III, in which $R^1$ and/or $R^2$ stand for an alkoxycarbonylalkyl radical, with amines of the general formula $HNR^{11}R^{12}$ in which $R^{11}$ and $R^{12}$ have the above-given meanings.

Compounds of general formula I or III, in which $R^1$ and/or $R^2$ stand for an N-unsubstituted aminoalkyl radical, are preferably prepared by the catalytic hydrogenation of compounds of general formula I or III, in which $R^1$ and/or $R^2$ stand for a cyanoalkyl or azidoalkyl radical. As catalyst, in the case of cyanoalkyl radicals there is preferably used Raney nickel and in the case of azidoalkyl radicals preferably palladium on active carbon. Compounds of general formula I or III, in which $R^1$ and/or $R^2$ stand for an amidinoalkyl radical, can also be prepared according to known methods from compounds of general formula I or III, in which $R^1$ and/or $R^2$ stand for a cyanoalkyl or carboxyalkyl radical.

N-unsubstituted aminoalkyl radicals $R^1$ and/or $R^2$ in compounds of general formula I or III can be alkylated or acylated according to known methods with the help of 1,1'-thiocarbonyldiimidazole to give isothiocyanatoalkyl radicals and with the help of 3,5-dimethyl-$N^2$-nitro-1-pyrazole-1-carboxamide to give (2-nitroguanidino)-alkyl radicals and can optionally be converted by other known methods into other functional modifications of an unsubstituted aminoalkyl group.

Hydroxyalkyl radicals $R^1$ and/or $R^2$ in compounds of general formula I or III can also be functionally modified according to known methods, for example by acylation to give acyloxyalkyl radicals or to give haloalkyl radicals or by reaction with arylsulphonic acid chlorides to give arylsulphonyloxyalkyl radicals.

Arylsulphonyloxyalkyl radicals and alkylsulphonyloxyalkyl radicals $R^1$ and/or $R^2$ in compounds of general formula I or III can be converted in known manner by reaction with potassium cyanide into cyanoalkyl radicals, by reaction with sodium azide into azidoalkyl radicals, by reaction with amines into aminoalkyl radicals or by reaction with thiourea into amidinothioalkyl radicals.

Alkylthioalkyl radicals $R^1$ and/or $R^2$ in compounds of general formula I or III can be oxidised to alkylsulphinylalkyl or alkylsulphonylalkyl radicals.

Further modifications of the radicals $R^1$ and/or $R^2$ in compounds of general formula I or III are also possible according to known methods.

In the same way as for the radicals $R^1$ and/or $R^2$ in compounds of general formula I or III, the radicals $R^3$ to $R^{10}$ in compounds of general formula I or III can if desired, also be functionally modified.

Thus, for example, radicals $R^3$ to $R^{10}$ which stand for nitro groups can be reduced by known methods to give radicals $R^3$ to $R^{10}$ which stand for amino groups.

In the same way, radicals $R^3$ to $R^{10}$ which stand for methoxy radicals can be converted by ether cleavage, for example with boron tribromide or pyridinium hydrochloride, or radicals $R^3$ and $R^{10}$ which stand for benzyloxy radicals can be converted by catalytic hydrogenation into radicals $R^3$ to $R^{10}$ which stand for hydroxyl groups.

Radicals $R^3$ to $R^{10}$ which stand for hydroxyl groups can subsequently again be alkylated, acylated or aminoalkylated. In the same way, radicals $R^3$ to $R^{10}$ which stand for amino groups can be alkylated or acylated.

Radicals $R^3$ to $R^{10}$ which stand for alkylthio radicals can be oxidised in known manner to give radicals $R^3$ to $R^{10}$ which stand for alkylsulphinyl or alkylsulphonyl radicals.

Compounds of general formula I or III, in which one or two of the radicals $R^3$ to $R^{10}$ stand for $C_1$–$C_4$-alkyl, $C_1$–$C_4$-acyl, chlorine, bromine or nitro, can also be prepared according to known methods of electrophilic aromatic substitution from compounds of general formula I or III, in which the radicals $R^3$ and $R^{10}$ in question stand for hydrogen atoms.

State of the Art

1) Imides of general formula I are known in which the radicals $R^1$ and $R^2$ stand for hydrogen atoms (see EP 0 269 025, compounds of general formula IV; J. Org. Chem., 1989, 54, 824; Angew. Chem., 1980, 92, 463; Tetrahedron Lett., 1983, 1441; St. J. Berthel and G. W. Gribble, 197th ACS National Meeting, Dallas, Tex., U.S.A., 1989, Abstract 116). Hitherto, no pharmacological or protein kinase-inhibiting actions have been described for these compounds.

2) Also known are indolocarbazole-N- and N,N'-glycosides of microbial or semi-synthetic origin which have been preponderantly described with anti-tumour action and the aglycones of which are encompassed by general formula I. However, it cannot be deduced from these publications that the aglycones of these indolocarbazole glycosides or the synthetic derivatives described in the present Application also possess pharmacological actions (for example U.S. Pat. No. 4,552,842; U.S. Pat. No. 4,524,145; EP 0 269 025; EP 0 388 962; EP 0 450 327; EP 0 445 736; JP 024571; WO 8907-105-A; JP 3295-589-A; WO 8807-045-A). An individual compound of synthetic origin related to these indolocarbazole glycosides, for which pharmacological actions are also given, is described in EP 0 410 389.

3) In the case of the present state of knowledge, it is to be regarded as being surprising that the compounds of general formula I according to the present invention are potent inhibitors of protein kinases, especially of protein kinase C and/or of myosin light chain kinase. From the literature (see Bio/Technology, 1990, 8, 132–135), it is known that N-glyccosidic indolocarbazole imides, such as rebeccamycin or AT 2433, in contradistinction to staurosporin, do not inhibit protein kinases. The authors conclude therefrom that the structure of the sugar residue is decisive for the inhibitory activity towards protein kinases (loc. cit., 734, 1st paragraph). In view of the prejudgement of the expert world, the expert would thus have had to assume that only N-glycosidic indolocarbazoles of the staurosporin type would represent a suitable starting point for the development of potent and selective protein kinase inhibitors. The synthetic development of such derivatives was, however, unsuccessful because of the absence of methods for the linkage of the indolocarbazole system with the glycoside radical. A total synthesis of staurosporin has not yet been accomplished. Non-glycosidic indolocarbazole imides would have the technical advantage that they are synthetically considerably more easily obtainable. Admittedly, attempts have not been lacking to develop non-glycosidic indolocarbazole imides as inhibitors of protein kinases. However, in the literature, it has been pointed out (see J. Biol. Chem., 1991, 266, 15771–15781) that the oxidative cyclisation of bis-indolyl-maleimides to give indolocarbazole imides involves a decrease of the inhibitory activity and a "complete loss of the specificity". That the compounds according to the present invention of general formula I prove to be potent and, in some cases, selective inhibitors of PKC and MLCK was, with this state of affairs, not to have been expected. Furthermore, in our test system, for compound 16 of the above-mentioned literature reference (J. Biol. Chem., loc. cit.), in our description we have, surprisingly, found that it is a potent MLC-kinase inhibitor which can, therefore, be considered for the potential pharmaceutical actions which we have claimed.

4) In EP 0 388 956, there is admittedly described a microbially-produced non-glycosidic indolocarbazole imide (BE-13193C) with antitumour action (formula I, $R^3=R^{10}-OH$, $R^1-R^2=R^4-R^9=H$). An inhibitory activity towards protein kinases is not known. According to the prior art, it was to have been assumed that the anti-tumour action, as in the case of rebeccamycin and similar compounds, comes about via a mechanism other than via the inhibition of protein kinases. Because of the claimed anti-tumour action for the compounds of general formula I, this compound is excluded from the general claim. Furthermore, N-glycosides of BE-13193C with anti-tumour action are known (see WO 9118003).

5) Cancer is a multifactorial faulty regulation of cell growth. The activation of PKC or the overexpression of this enzyme has basically been held to be responsible for certain tumours. For the purpose of a specific therapy of such tumours, there is a need for potent and selective protein kinase C inhibitors. In this regard, the compounds according to the present invention represent an advance with regard to the known indolocarbazole derivatives with non-specific anti-tumour action.

6) Some indolocarbazole derivatives of general formula I are described in the Patent Applications EP10 0 328 000 and EP 0 370 236 as intermediates for the compounds according to the present invention but without mention of pharmacological actions or of protein kinase-inhibiting properties.

Biological data of compounds of general formula I

1. Inhibition of the enzyme MLC kinase (EC 3.6.1.3; kinase of the light myosin chain; myosin light-chain kinase).

MLC kinase is an important key enzyme for the regulation of smooth muscle tone (see, for example, R. S. Adelstein and E. Eisenberg, Ann. Rev. Biochem., 49, 921–956, 1980). Since an activation of the enzyme leads to a contraction of the smooth muscle, it is to be expected that inhibitors of MLC kinase weaken the smooth muscle contraction and, in vivo, lead to a lowering of the blood pressure. In recent years, some inhibitors of MLC kinase have already been described in the literature (see S. Nakanishi et al., J. Biol. Chem., 263, 6215–6219, 1988; and Mol. Pharmacol., 31, 482–488, 1990) but an unambiguous anti-hypertensive action has hitherto not been demonstrated.

The inhibition of MLC kinase was measured in an in vitro enzyme test. For this purpose, with reference to Ngai et al. (Biochem. J., 218, 863–870, 1984), MLC kinase was purified from chicken stomach. The light myosin chain was also obtained from chicken stomach (see D. R. Hathaway and J. R. Haeberle, Anal. Biochem., 135, 37–43, 1983).

The enzyme activity was determined via the incorporation of $^{32}$P-labelled phosphate under the following conditions: the reaction batch of 200 μl contained 50 mM MOPS-NaOH, pH 7.2, 5 mM magnesium chloride, 100 μM calcium chloride, 100 nM calmodulin, 1 mM DTT, 250 μM ATP, as well as 20 μM myosin light chain. The reaction was initiated by the addition of 1 nM MLC kinase. After incubation for 20 minutes at 30° C., the reaction was stopped with TCA and the samples then filtered off. The phosphate incorporation took place by means of Cerenkov counting of the filter.

The following Table I shows the results from this test for a number of Examples.

In order to ascertain whether it is a question of a selective inhibition of MLC kinase, the compounds were also investigated in other enzyme tests for protein kinase, including tests for protein kinase C. The results from the PKC test are also given in the following Table I. Furthermore, the Table contains selectivity factors which were calculated by the determination of the ratios of the $IC_{50}$ values. From these data, it follows that, in particular, Examples 4, 4a, 4b, 5, 7b, 7c, 11c and 11d can be regarded as being potent and selective inhibitors of MLC kinase, whereas, for example, Example 1 is a potent and selective protein kinase C inhibitor.

For Examples 5, 7c and 11d, besides potency and selectivity in the kinase test, in vivo a dosage-dependent anti-hypertensive action could be demonstrated. As test model, there was used the narcotised, spontaneously hypertensive rat (SHR). After intravenous administration of the inhibitor of MLC kinase, in each case 60 minutes after the administration of the compound, there were found the reductions of the average arterial blood pressure set out in the following Table 2. An influencing of the heart frequency was scarcely observable (cf. Table 2).

TABLE 1

Inhibition of myosin light-chain kinase and of protein kinase C by indolocarbazole imides

| Example | inhibition of the protein kinases ($IC_{50}$; μM) | | ratio of $IC_{50}$ C-kinase/ $IC_{50}$ MLC-kinase |
|---|---|---|---|
| | MLC-kinase | C-kinase | |
| 1 | 0.2 | 0.0015 | 0.008 |
| 1a | 0.055 | 0.038 | 0.7 |
| 1b | 0.049 | 0.035 | 0.7 |
| 1c | 0.18 | 0.019 | 0.1 |
| 1d | 0.062 | 0.035 | 0.6 |
| 1e | 0.017 | 0.014 | 0.8 |
| 1g | 0.022 | 0.036 | 1.6 |
| 1h | 0.024 | 0.024 | 1 |
| 1j | 0.045 | 0.500 | 11.1 |
| 1k | 0.061 | 0.44 | 7.2 |
| 1l | 0.13 | 0.05 | 0.4 |
| 1n | 0.032 | 0.020 | 0.6 |
| 1o | 0.017 | 0.0067 | 0.4 |
| 1q | 0.032 | 0.0047 | 0.15 |
| 1r | 0.029 | 0.017 | 0.6 |
| 1s | 0.033 | 0.024 | 0.7 |
| 1u | 0.54 | 4.7 | 8.7 |
| 1x | 0.0072 | 0.052 | 7.2 |
| 1y | 0.0076 | 0.031 | 4.1 |
| 1z | 0.020 | 0.026 | 1.3 |
| 2 | 0.019 | 0.024 | 1.3 |
| 2a | 0.018 | 0.031 | 1.7 |
| 2b | 0.032 | 0.230 | 7.2 |
| 2c | 0.0061 | 0.014 | 2.3 |
| 2d | 0.016 | 0.038 | 2.4 |
| 2e | 0.0057 | 0.007 | 1.3 |
| 2f | 0.010 | 0.0042 | 0.4 |

TABLE 1-continued

Inhibition of myosin light-chain kinase and of protein kinase C by indolocarbazole imides

| Example | inhibition of the protein kinases ($IC_{50}$; μM) MLC-kinase | C-kinase | ratio of $IC_{50}$ C-kinase/ $IC_{50}$ MLC-kinase |
|---|---|---|---|
| 2g | 0.0050 | 0.040 | 8 |
| 3 | 0.076 | 0.190 | 2.5 |
| 4 | 0.0012 | 0.039 | 33 |
| 4a | 0.0049 | 0.360 | 74 |
| 4b | 0.0015 | 0.034 | 23 |
| 4c | 0.021 | 0.053 | 2.5 |
| 5 | 0.0037 | 0.087 | 24 |
| 6 | 0.17 | 0.50 | 2.9 |
| 7 | 0.040 | 0.38 | 9.5 |
| 7a | 0.052 | 0.53 | 10 |
| 7b | 0.0087 | >10(46) | >1149 |
| 7c | 0.023 | >10(22) | >435 |
| 7d | 0.0084 | 0.025 | 3.0 |
| 7g | 0.110 | 0.042 | 0.4 |
| 8 | 0.0052 | 0.059 | 11.3 |
| 10 | 0.12 | 0.021 | 0.2 |
| 10a | 0.37 | 0.12 | 0.3 |
| 10b | 0.12 | 0.004 | 0.033 |
| 11a | 0.42 | 1.9 | 4.5 |
| 11b | 0.060 | 0.28 | 4.7 |
| 11c | 0.086 | 4.0 | 47 |
| 11d | 0.021 | >10(45) | >476 |
| 11e | 0.60 | >10(10) | >17 |
| 11g | 0.37 | 4.6 | 12 |

TABLE 2

Anti-hypertensive action of inhibitors of MLC-kinase
Model: Narcotised SHRs, i.v. administration
(average values ± SD)

| Example | dose (mg/kg) | reduction of the average arterial blood pressure (%) | reduction of the heart frequency (%) | number of experiments |
|---|---|---|---|---|
| 5 | 1 | 15 ± 5 | 3 ± 3 | 6 |
|  | 3 | 23 ± 3 | 7 ± 4 | 5 |
|  | 10 | 40 ± 8 | 4 ± 3 | 6 |
| 7c | 3 | 10 ± 7 | 7 ± 3 | 6 |
|  | 10 | 23 ± 2 | 8 ± 2 | 6 |
| 11d | 3 | 16 ± 3 | 6 ± 2 | 6 |
|  | 10 | 35 ± 5 | 10 ± 3 | 6 |

2. In vitro anti-tumour action.

The enzyme protein kinase C plays an important part in the case of the regulation of cell growth and differentiation. On the basis of this property, the inhibition of PKC is considered as being a new therapeutic principle for tumour therapy (see A. Gescher and I. L. Dale, Anti-Cancer Drug Design, 4, 93–105, 1989; H. Grunicke et al., Adv. Enzyme Regulation, 28, 201–216, 1989).

One possibility to test in vitro the anti-tumour action of compounds is the colony test (see H. H. Fiebig et al., Eur. J. Canc. Clin. Onc., 23, 931–948, 1987). For this test, human tumour cells are kept as solid tumour by passage on the nude mouse. For the test, an individual cell suspension is prepared and the cells then plated out in dishes containing soft agar. Under these conditions, the tumour cells multiply and form colonies. Compounds with anti-tumour action, for example adriamycin, are able to prevent this colony formation.

For Examples 2c, 7g and 10, it was possible to show that, in the case of certain tumour types, the growth of the tumour cells can be inhibited depending upon the concentration. The following Table 3 shows these findings using Example 2c as an example.

TABLE 3

Inhibition of colony formation of human tumour cells by Example 2c

| Tumour type | Inhibition of the colony formation (%) in the case of a substance concentration (M) of | | | |
|---|---|---|---|---|
|  | $10^{-7}$ | $10^{-6}$ | $10^{-5}$ | $IC_{50}$ (μM) |
| colon | 8 | 37 | 94 | 1.7 |
| colorectal 1 | 0 | 8 | 62 | 6.0 |
| gastric 1 | 29 | 47 | 99 | 1.2 |
| gastric 2 | 65 | 66 | 77 | <0.1 |
| lung (large cell) | 97 | 100 | 100 | <0.1 |
| lung (small cell 1) | 82 | 97 | 97 | <0.1 |
| melanoma 1 | 48 | 81 | 89 | 0.12 |
| melanoma 2 | 90 | 99 | 97 | <0.1 |
| melanoma 3 | 38 | 76 | 73 | 0.21 |
| ovarian 1 | 40 | 75 | 96 | 0.2 |
| ovarian 2 | 5 | 33 | 75 | 2.6 |
| ovarian 3 | 74 | 94 | 99 | <0.1 |
| pancreas 1 | 38 | 44 | 83 | 1.5 |
| prostata 1 | 29 | 99 | 98 | 0.2 |

3. Anti-HIV action.

According to recent findings, protein kinase C participates in the reactivation of HIV viruses from the latent stage (see A. L. Kinter et al., J. Virol., 64, 4306–4312, 1990).

In the case of the establishment of this hypothesis, use was made of the promonocytic cell line U1.

Without stimulation, no formation of HIV can be measured in these cells but, after 15 minutes stimulation with the phorbol ester PMA, it results in a massive production of HIV. If, one hour before the PMA stimulation, the cell is incubated with the PKC inhibitor H-7, whereby, after the stimulation, there follows a further 48 hours incubation with the inhibitor, then it is shown that the production of HIV can be completely suppressed.

Some of the PKC inhibitors according to the present invention were investigated in this model. As a measure for the HIV production, either with the help of an ELISA test there was determined the viral protein p24 or with the help of an indicator cell, there was measured the HIV-induced formation of syncytia (giant cells produced by the fusion of individual cells).

With both test methods, an anti-HIV action could be demonstrated for Examples 1 and 2c. The results obtained are summarised in the following Table 4. On the basis of control experiments, it could be shown that the anti-HIV action did not come about due to a cytotoxic action.

TABLE 4

Inhibition of the phorbol ester-induced HIV reactivation by PKC inhibitors

| | inhibition of the HIV production $IC_{50}$ (nM) | |
|---|---|---|
| Example | p24 expression (average value ± SD; n = 3) | syncytia formation (average value; n = 2) |
| 1 | 118 ± 98 | 28 |
| 2c | 36 ± 15 | 29 |

The following Examples are given for the purpose of illustrating the present invention:

EXAMPLE 1

13-(2-Cyanoethyl)-6,7,12,13-tetrahydro-3-methoxy-12-methyl-5,7-dioxo-5H-indolo[2,3-a]pyrrolo[3,4-c]-carbazole

500 mg (1.18 mmol) 3-[1-(2-cyanoethyl)-5-methoxy-3-indolyl]-4-(1-methyl-3-indolyl)-1H-pyrrole-2,5-dione in 50 ml toluene are heated under reflux for 30 minutes with 225 mg (1.18 mmol) p-toluenesulphonic acid hydrate and 315 mg (1.39 mmol) 2,3-dichloro-5,6-dicyano-p-benzoquinone (DDQ). After cooling, the reaction mixture is evaporated in a vacuum and the residue is stirred with 100 ml 0.1N sodium hydroxide solution. The aqueous suspension is saturated with sodium chloride and extracted twice with, in each case, 100 ml tetrahydrofuran. The tetrahydrofuran solutions are washed twice with, in each case, 100 ml saturated sodium chloride solution. The residue is chromatographed on silica gel with toluene/acetone (4:1 v/v). The fraction with the Rf 0.3 is isolated, stirred up with diisopropyl ether and the crystals formed are filtered off. There are obtained 270 mg (54% of theory) 13-(2-cyanoethyl)-6,7,12,13-tetrahydro-3-methoxy-12-methyl-5,7-dioxo-5H-indolo[2,3-a]pyrrolo[3,4-c]carbazole in the form of yellow crystals which decompose from about 260° C. with the evolution of gas.

The 3-[1-(2-cyanoethyl)-5-methoxy-3-indolyl]-4-(1-methyl-3-indolyl)-1H-pyrrole-2,5-dione used as starting material (dark yellow amorphous powder which decomposes from about 200° C.) is prepared analogously to EP 0 328 026 from 1-(2-cyanoethyl)-5-methoxy-indole and 1-methyl-3-indolylacetic acid. 1-(2-Cyanoethyl)-5-methoxyindole is prepared in quantitative yield by the base-catalysed (DBU) addition of acrylonitrile to 5-methoxyindole in acetonitrile.

The following compounds are obtained in an analogous manner:

1a) 12-(2-cyanoethyl)-6,7,12,13-tetrahydro-13-methyl-5,7-dioxo-5H-indolo[2,3-a]pyrrolo[3,4-c]carbazole; yellow crystals which decompose from about 200° C.

1b) 12-(2-cyanoethyl)-6,7,12,13-tetrahydro-3-methoxy-13-methyl-5,7-dioxo-5H-indolo[2,3-a]pyrrolo[3,4-c]-carbazole; yellow crystals which decompose from about 300° C. The 3-[1-(2-cyanoethyl)-3-indolyl]-4-(5-methoxy-1-methyl-3-indolyl)-1H-pyrrol-2,5-dione used as starting material (pale red amorphous powder, decomp. point about 250–258° C.) is prepared analogously to EP 0 328 026 from 1-(2-cyanoethyl)-indole and 5-methoxy-1-methyl-3-indolylacetic acid.

1c) 12-(2-cyanoethyl)-6,7,12,13-tetrahydro-3,9-dimethoxy-13-methyl-5,7-dioxo-5H-indolo[2,3-a]pyrrolo[3,4-c]-carbazole; yellow crystals which decompose from about 210° C. The 3-[1-(2-cyanoethyl)-5-methoxy-3-indolyl]-4-(5-methoxy-1-methyl-3-indolyl)-1H-pyrrol-2,5-dione used as starting material (orange-red amorphous powder; decomp. point about 255–263° C.) is prepared analogously to EP 0 328 026 from 1-(2-cyanoethyl)-5-methoxy-indole and 5-methoxy-1-methyl-3-indolylacetic acid.

1d) 12-(3-cyano-2-propyl)-6,7,12,13-tetrahydro-13-methyl-5,7-dioxo-5H-indolo[2,3-a]pyrrolo[3,4-c]carbazole; yellow crystals which decompose from about 270° C. The 3-[1-(3-cyano-2-propyl)-3-indolyl]-4-(1-methyl-3-indolyl)-1H-pyrrol-3,5-dione used as starting material (red amorphous powder; decomp. point about 218–226° C.) is prepared analogously to EP 0 328 026 from 1-(3-cyano-2-propyl)-indole and 1-methyl-3-indolylacetic acid. 1-(3-Cyano-2-propyl)-indole is prepared in low yield by the base-catalysed (DBU) addition of crotonitrile to indole in acetonitrile.

1e) 12-cyanomethyl-6,7,12,13-tetrahydro-13-methyl-5,7-dioxo-5H-indolo[2,3-a]pyrrolo[3,4-c]carbazole; yellow amorphous powder which decomposes from about 330° C. The 3-(1-cyanomethyl-3-indolyl)-4-(1-methyl-3-indolyl)-1H-pyrrol-2,5-dione used as starting material (red amorphous powder) is prepared analogously to EP 0 328 036 from 1-cyanomethylindole (J.A.C.S., 1975, 97, 4098) and 1-methyl-3-indolylacetic acid.

1f) 3-chloro-13-(2-cyanoethyl)-6,7,12,13-tetrahydro-12-methyl-5,7-dioxo-5H-indolo[2,3-a]pyrrolo[3,4-c]-carbazole; yellow amorphous powder; m.p. 281–286° C. The 3-[5-chloro-1-(2-cyanoethyl)-3-indolyl]-4-(1-methyl-3-indolyl)-1H-pyrrol-2,5-dione used as starting material (orange-coloured amorphous powder; m.p. 240–243° C.) is prepared analogously to EP 0 328 026 from 5-chloro-1-(2-cyanoethyl)-indole and 1-methyl-3-indolylacetic acid. 5-Chloro-1-(2-cyanoethyl)-indole is prepared by base-catalysed (DBU) addition of acrylonitrile to 5-chloro-indole in acetonitrile.

1g) 12-(3-cyanopropyl)-6,7,12,13-tetrahydro-13-methyl-5,7-dioxo-5H-indolo[2,3-a]pyrrolo[3,4-c]carbazole; yellow crystals; m.p. 259–261° C. The 3-[1-(3-cyanopropyl)-3-indolyl]-4-(1-methyl-3-indolyl)-1H-pyrrol-2,5-dione used as starting material (dark red amorphous powder) is prepared analogously to EP 0 328 026 from 1-(3-cyanopropyl)-indole and 1-methyl-3-indolylacetic acid. 1-(3-cyanopropyl)-indole is prepared from 1-(2-cyanoethyl)-indole (synthesis of 1-[3-(4-methylphenyl-sulphonyloxy)-propyl]-indole according to J. Chem. Soc. 1967, 2599 and J.A.C.S., 1975, 97, 4095, and reaction with potassium cyanide in dimethylformamide to give 1-(3-cyanopropyl)-indole).

1h) 12-(3-cyanopropyl)-6,7,12,13-tetrahydro-3-methoxy-13-methyl-5,7-dioxo-5H-indolo[2,3-a]pyrrolo[3,4-c]-carbazole; yellow amorphous powder which decomposes at about 265° C. The 3-[1-(3-cyanopropyl)-3-indolyl]-4-(5-methoxy-1-methyl-3-indolyl)-1H-pyrrol-2,5-dione used as starting material (red amorphous powder of decomp. point 275–279° C.) is prepared analogously to EP 0 328 026 from 1-(3-cyanopropyl)-indole and 5-methoxy-1-methyl-3-indolylacetic acid.

1i) 12-[3-(4-methylphenylsulphonyloxy)-propyl]-6,7,12,13-tetrahydro-13-methyl-5,7-dioxo-5H-indolo-[2,3-a]pyrrolo[3,4-c]carbazole; yellow amorphous powder which decomposes from about 195° C. The 3-[1-[3-(4-methylphenylsulphonyloxy)-propyl]]-4-(1-methyl-3-indolyl)-1H-pyrrolo-2,5-dione used as starting Material (red amorphous powder) is prepared analogously to EP 0 328 026 from 1-[3-(4-methylphenylsulphonyloxy)-propyl]-indole and 1-methyl-3-indolylacetic acid.

1j) 12-(3-dimethylaminopropyl)-6,7,12,13-tetrahydro-13-methyl-5,7-dioxo-5H-indolo[2,3-a]pyrrolo[3,4-c]-carbazole; yellow crystals; m.p. 236–243° C. Prepared analogously to Example 1 but with 2 equivalents of p-toluenesulphonic acid hydrate and 2 equivalents of DDQ. The 3-[1-(3-dimethylaminopropyl)-3-indolyl]-4-(1-methyl-3-indolyl)-1H-pyrrol-2,5-dione used as starting material is prepared analogously to EP 0 328 026 from 1-(3-dimethylaminopropyl)-indole and 1-methyl-3-indolylacetic acid. Example 1j) can also be prepared by the reaction of Example 1i) with dimethylamine in the usual way.

1k) 13-(3-Dimethylaminopropyl)-6,7,12,13-tetrahydro-3-methoxy-12-methyl-5,1-dioxo-5H-indolo[2,3-a]pyrrolo-[3,4-c]carbazole; yellow crystals; m.p. 240–246° C. The 3-[1-(3-dimethylaminopropyl)-5-methoxy-5-methoxy-3-indolyl]-4-(1-methyl-3-indolyl)-1H-pyrrol-2,5-dione used as starting material is prepared analogously to EP 0 328 026 from 1-(3-dimethylaminopropyl)-

5-methoxyindole (prepared analogously to Synthesis 1984, 29) and 1-methyl-3-indolylacetic acid.

1l) 12-(3-azidopropyl)-6,7,12,13-tetrahydro-13-methyl-5,7-dioxo-5H-indolo[2,3-a]pyrrolo[3,4-c]carbazole; yellow crystals which decompose from about 220° C. The 3-[1-(3-azidopropyl)-3-indolyl]-4-(1-methyl-3-indolyl)-1H-pyrrol-2,5-dione used as starting material is prepared according to EP 0 328 026 from 1-(3-bromo-propyl)-indole and 1-methyl-3-indolylacetic acid. Example 1l) can also be prepared by the reaction of Example 1i) with sodium azide in dimethylformamide.

1m) 12-(2-azidoethyl)-6,7,12,13-tetrahydro-13-methyl-5,7-dioxo-5H-indolo[2,3-a]pyrrolo[3,4-c]carbazole; yellow crystals; decomp. point 237–241° C. The 3-[1-(2-azidoethyl)-3-indolyl]-4-(1-methyl-3-indolyl)-1H-pyrrol-2,5-dione used as starting material is prepared analogously to Example 1l) and EP 0 328 026 from 1-(2-chloroethyl)-indole and 1-methyl-3-indolylacetic acid.

1n) 3-chloro-13-(2-cyanoethyl)-6,7,12,13-tetrahydro-9-methoxy-12-methyl-5,7-dioxo-5H-indolo[2,3-a]pyrrolo-[3,4-a]carbazole; yellow amorphous powder; m.p. >300° C. The 3-[5-chloro-1-(2-cyanoethyl)-3-indolyl]-4-(5-methoxy-1-methyl-3-indolyl)-1H-pyrrol-2,5-dione used as starting material is prepared analogously to EP 0 328 026 from 5-chloro-1-(2-cyanoethyl)-indole and 5-methoxy-1-methyl-3-indolylacetic acid.

1o) 13-(2-cyanoethyl)-6,7,12,13-tetrahydro-2,3-dimethoxy-12-methyl-5,7-dioxo-5H-1-indolo[2,3-a]pyrrolo-[3,4-c]carbazole; yellow crystals; m.p. 293–296° C. The 3-[1-(2-cyanoethyl)-5,6-dimethoxy-3-indolyl]-4-(1-methyl-3-indolyl)-1H-pyrrol-2,5-dione used as starting material is prepared analogously to EP 0 328 026 from 1-(2-cyanoethyl)-5,6-dimethoxyindole and 1-methyl-3-indolylacetic acid. 1-(2-cyanoethyl)-5,6-dimethoxyindole is prepared by the base-catalysed (DBU) addition of acrylonitrile to 5,6-dimethoxyindole in acetonitrile.

1p) 13-(2-cyanoethyl)-6,7,12,13-tetrahydro-12-methyl-5,7-dioxo-3-n-propoxy-5H-indolo[2,3-a]pyrrolo[3,4-c]-carbazole; yellow amorphous powder; m.p. 255–258° C.

1q) 13-(3-cyanopropyl)-6,7,12,13-tetrahydro-3-methoxy-12-methyl-5,7-dioxo-5H-indolo[2,3-a]pyrrolo[3,4-c]-carbazole; yellow amorphous powder which decomposes at about 280–285° C. The 3-[1-(3-cyanopropyl)-5-methoxy-3-indolyl]-4-(1-methyl-3-indolyl)-1H-pyrrol-2,5-dione used as starting material is prepared analogously to EP 0 328 026 from 1-(3-cyanopropyl)-5-methoxyindole and 1-methyl-3-indolylacetic acid. 1-(3-Cyanopropyl)-5-methoxyindole is prepared from 1–10 (3-cyanoethyl)-5-methoxyindole analogously to 1-(3-cyanopropyl)-indole (see Example 1g).

1r) 12-(3-cyanopropyl)-6,7,12,13-tetrahydro-3,9-dimethoxy-13-methyl-5,7-dioxo-5H-indolo[2,3-a]pyrrolo-[3,4-c]carbazole; yellow amorphous powder which decomposes at about 285–290° C. The 3-[1-(3-cyanopropyl)-5-methoxy-3-indolyl]-4-(5-methoxy-1-methyl-3-indolyl)-1H-pyrrol-2,5-dione used as starting material is prepared analogously to EP 0 328 026 from 1-(3-cyano-propyl)-5-methoxyindole and 5-methoxy-1-methyl-3-indolylacetic acid.

1s) 13-(2-cyanoethyl)-6,7,12,13-tetrahydro-2,3,9-trimethoxy-12-methyl-5,7-dioxo-5H-indolo[2,3-a]pyrrolo-[3,4-c]carbazole; brown amorphous powder which decomposes from about 275° C. The 3-[1-(2-cyanoethyl)-5,6-dimethoxy-3-indolyl]-4-(5-methoxy-1-methyl-3-indolyl)-1H-pyrrol-2,5-dione used as starting material is prepared analogously to EP 0 328 026 from 1-(2-cyano-ethyl)-5,6-dimethoxyindole and 5-methoxy-1-methyl-3-indolylacetic acid. 1-(2-cyanoethyl)-5,6-dimethoxy-indole is prepared by the base-catalysed (DBU) addition of acrylonitrile to 5,6-dimethoxyindole in acetonitrile.

1t) 13-(2-cyanoethyl)-6,7,12,13-tetrahydro-1-methoxy-12-methyl-5,7-dioxo-5H-indolo[2,3-a]pyrrolo[2,3-c]-carbazole; yellow amorphous powder; m.p. >300° C. The 3-[1-(2-cyanoethyl)-7-methoxy-3-indolyl]-4-(1-methyl-3-indolyl)-1H-pyrrol-2,5-dione used as starting material is prepared analogously to EP 0 328 026 from 1-(2-cyanoethyl)-7-methoxyindole and 1-methyl-3-indolylacetic acid. 1-(2-Cyanoethyl)-7-methoxyindole is prepared by the base-catalysed (DBU) addition of acrylonitrile to 1-methoxyindole in acetonitrile.

1u) 13-(2-cyanoethyl)-6,7,12,13-tetrahydro-2-methoxy-12-methyl-5,7-dioxo-5H-indolo[2,3-a]pyrrolo[3,4-c]-carbazole; brown amorphous powder which decomposes from about 200° C. The 3-[1-(2-cyanoethyl)-6-methoxy-3-indolyl]-4-(1-methyl-3-indolyl)-1H-pyrrol-2,5-dione used as starting material is prepared analogously to EP 0 328 026 from 1-(2-cyanoethyl)-6-methoxyindole and 1-methyl-3-indolylacetic acid. 1-(2-Cyanoethyl)-6-methoxyindole is prepared by the base-catalysed (DBU) addition of acrylonitrile to 6-methoxyindole in acetonitrile.

1v) 12-(4-azidobutyl)-6,7,12,13-tetrahydro-13-methyl-5,7-dioxo-5H-indolo[2,3-a]pyrrolo[3,4-c]carbazole; yellow amorphous powder; m.p. 186–188° C. The 3-[1-(4-azidobutyl)-3-indolyl]-4-(1-methyl-3-indolyl)-1H-pyrrol-2,5-dione used as starting material is prepared analogously to EP 0 328 026.

1w) 12-(5-azidopentyl)-6,7,12,13-tetrahydro-13-methyl-5,7-dioxo-5H-indolo[2,3-a]pyrrolo[3,4-c]carbazole; yellow amorphous powder; m.p. 165–170° C. The 3-[1-(5-azidobutyl)-3-indolyl]-4-(1-methyl-3-indolyl)-1H-pyrrol-2,5-dione used as starting material is prepared analogously to EP 0 328 026.

1x) 12-(2-dimethylaminoethyl)-6,7,12,13-tetrahydro-13-methyl-5,7-dioxo-5H-indolo[2,3-a]pyrrolo[3,4-c]-carbazole; yellow amorphous powder which decomposes from about 260° C. Prepared analogously to Example 1j). The 3-[1-(2-dimethylaminoethyl)-3-indolyl]-4-(1-methyl-3-indolyl)-1H-pyrrolaminoethyl)- 3-indolyl]-4-(1-methyl-3-indolyl)-1H-pyrrol-2,5-dione used as starting material is prepared analogously to EP 0 328 026 from 1-(2-dimethylaminoethyl)-indole and 1-methyl-3-indolylacetic acid.

1y) 12-(3-dimethylaminopropyl)-6,7,12,13-tetrahydro-3-methoxy-13-methyl-5,7-dioxo-5H-indolo[2,3-a]pyrrolo-[3,4-c]carbazole; yellow amorphous powder; m.p. 221–227° C. The 3-[1-(2-dimethylaminopropyl)-3-indolyl]-4-(5-methoxy-1-methyl-3-indolyl)-1H-pyrrol-2,5-dione used as starting material is prepared analogously to EP 0 328 026 from 1-(3-dimethylaminopropyl)-indole and 5-methoxy-1-methyl-3-indolylacetic acid.

1z) 13-(3-dimethylaminopropyl)-6,7,12,13-tetrahydro-2,3-dimethoxy-12-methyl-5,7-dioxo-5H-indolo[2,3-a]-pyrrolo[3,4-c]carbazole; yellow amorphous powder; m.p. 190–196° C. The 3-[5,6-dimethoxy-1-(3-dimethylamino-5 propyl)-3-indolyl]-4-(1-methyl-3-indolyl)-1H-pyrrol-2,5-dione used as starting material is prepared analogously to EP 0 328 026 from 5,6-dimethoxy-1-(3-dimethylaminopropyl)-indole and 1-methyl-3-indolylacetic acid.

1aa) 12-epoxymethyl-6,7,12,13-tetrahydro-13-methyl-5,7-dioxo-5H-indolo[2,3-a]pyrrolo[3,4-c]carbazole; brown amorphous powder; m.p. 142–148° C. The 3-[1- epoxymethyl-3-indolyl]-4-(1-methyl-3-indolyl)-1H-pyrrol-2,5-dione used as starting material is prepared analogously to EP 0 328 026 from 1-epoxymethylindole and 1-methyl-3-indolylacetic acid.

1ab) (+)-12-(3-chloro-2-hydroxy-1-propyl)-6,7,12,13-tetrahydro-13-methyl-5,7-dioxo-5H-indolo[2,3-a]pyrrolo-[3,4-c]carbazole; yellow amorphous powder; m.p. 238–254° C. Prepared from Example 1aa) by reaction with hydrogen chloride or as by-product in the preparation of Example 1aa).

EXAMPLE 2

13-(2-Cyanoethyl)-6,7,12,13-tetrahydro-3-hydroxy-12-methyl-5,7-dioxo-5H-indolo[2,3-a]pyrrolo[3,4-c]-carbazole 200 mg (0.45 mmol) 13-(2-cyanoethyl)-6,7,12,13-tetrahydro-3-methoxy-12-methyl-5,1-dioxo-5H-indolo-[2,3-a]pyrrolo[3,4-c]carbazole (Example 1) in 15 ml dichloromethane are cooled to −10° C. and 0.1 ml (0.7 mmol) of a 1M solution of boron tribromide in dichloromethane added dropwise thereto. Since, after 3 hours at −10° C., no reaction is shown (TLC), 1.4 ml of the 1M solution of boron tribromide are again added thereto, followed by stirring for 16 hours at 20° C. 100 ml of water and 100 ml tetrahydrofuran are added thereto and the organic phase is separated off, washed with 100 ml of water and dried over anhydrous sodium sulphate. After filtration and evaporation, the residue is first chromatographed with dichloromethane/methanol (95:5 v/v) and then again with toluene/tetrahydrofuran (4:1 v/v). The fraction with the Rf 0.3 in toluene/tetrahydrofuran (2:1 v/v) is isolated, stirred with diisopropyl ether/acetone and the crystals formed are filtered off. 13-(2-Cyanoethyl)-6,7,12,13-tetrahydro-3-hydroxy-12-methyl-5,7-dioxo-5H-indolo[2,3-a]pyrrolo[3,4-c]carbazole is obtained in the form of yellow crystals which decompose from about 315° C.

The following compounds are obtained in an analogous manner:

2a) 12-(2-cyanoethyl)-6,7,12,13-tetrahydro-3-hydroxy-13-methyl-5,7-dioxo-5H-indolo[2,3-a]pyrrolo[3,4-c]-carbazole; yellow amorphous powder which decomposes from about 320° C. (prepared from Example 1b).

2b) 13-(2-cyanoethyl)-6,7,12,13-tetrahydro-2,3-dihydroxy-12-methyl-5,7-dioxo-5H-indolo[2,3-a]pyrrolo[3,4-c]-carbazole; orange amorphous powder which decomposes from about 210° C. (prepared from Example 1o).

2c) 12-(3-dimethylaminopropyl)-6,7,12,13-tetrahydro-3,9-dihydroxy-5,1-dioxo-5H-indolo[2,3-a]pyrrolo[3,4-c]-carbazole; dark yellow crystals which decompose from about 200° C. (prepared from Example 7).

2d) 12-(3-dimethylaminopropyl)-6,7,12,13-tetrahydro-3(9)-hydroxy-9(3)-methoxy-5,7-dioxo-5H-indolo[2,3-a]pyrrolo[3,4-c]carbazole; light brown amorphous powder which decomposes from about 195° C. (approx. 2:1 regioisomeric mixture, prepared from Example 7).

2e) 6,7,12,13-tetrahydro-3,9-dihydroxy-5,1-dioxo-5H-indolo[2,3-a]pyrrolo[3,4-c]carbazole; light brown amorphous powder; m.p. >350° C. (prepared from 6,7,12,13-tetrahydro-3,9-dimethoxy-5,7-dioxo-5H-indolo[2,3-a]-pyrrolo[3,4-c]carbazole; see Example 11d).

2f) 12-(2-cyanoethyl)-6,7,12,13-tetrahydro-3,9-dihydroxy-13-methyl-5,7-dioxo-5H-indolo[2,3-a]pyrrolo-[3,4-c]carbazole; dark yellow amorphous powder which decomposes from about 210° C. (prepared from Example 1c).

2g) 13-(3-dimethylaminopropyl)-6,7,12,13-tetrahydro-3-hydroxy-12-methyl-5,7-dioxo-5H-indolo[2,3-a]pyrrolo 25 [3,4-c]carbazole; yellow amorphous powder; m.p.270–273° C. (prepared from Example 1k).

2h) 12-(3-diisopropylaminopropyl)-6,7,12,13-tetrahydro-3-hydroxy-13-methyl-5,1-dioxo-5H-indolo[2,3-a]pyrrolo-[3,4-c]carbazole; yellow crystals; m.p. 303–306° C.

EXAMPLE 3

12-(3-Dimethylaminopropyl)-6,7,12,13-tetrahydro-13-methyl-5,7-dioxo-5H-indolo[2,3-a]pyrrolo[3,4-c]-carbazole; methiodide 57.6 mg (0.136 mmol) 12-(3-Dimethylaminopropyl)-6,7,12,13-tetrahydro-13-methyl-5,7-dioxo-5H-indolo-[2,3-a]pyrrolo[3,4-c]carbazole (Example 1j) are dissolved in 50 ml ethyl acetate, mixed with 3 drops of methyl iodide and stirred for 16 hours at 20° C. The crystals which precipitate out are filtered off, washed with ethyl acetate and dried. The methiodide is obtained in the form of yellow crystals which decompose from about 280° C. TLC: silica gel; butyl acetate/ethyl acetate/water (3:2:1 v/v/v), Rf=0.45.

EXAMPLE 4

12-(3-Aminopropyl)-6,7,12,13-tetrahydro-13-methyl-5,7-dioxo-5H-indolo[2,3-a]pyrrolo[3,4-c]carbazole 760 mg (1.94 mmol) 12-(2-Cyanoethyl)-6,7,12,13-tetrahydro-13-methyl-5,7-dioxo-5H-indolo[2,3-a]-pyrrolo [3,4-c]carbazole (Example 1a) in 100 ml methanol are hydrogenated in the presence of 500 mg Raney nickel at 60° C. and 50–65 bar pressure for 20 hours in an autoclave. The reaction mixture is evaporated, the residue is taken up in 100 ml dimethylformamide, filtered off from the catalyst and again evaporated in a vacuum. The residue is chromatographed on silica gel with dichloromethane/methanol saturated with ammonia (95:5 v/v). The fraction with the Rf of 0.1 is isolated, stirred with ethanol and the undissolved product is filtered off. 12-(3-aminopropyl)-6,7,12,13-tetrahydro-13-methyl-5,7-dioxo-5H-indolo[2,3-a]pyrrolo[3,4-c]-carbazole is obtained as an amorphous yellow powder which decomposes from about 250° C.

The product of Example 4 is also obtained by the catalytic hydrogenation of the product of Example 11 in the presence of 10% palladium on active carbon in ethyl acetate at normal pressure and at 20° C.

The following compounds are obtained in analogous manner:

4a) 13-(3-aminopropyl)-6,7,12,13-tetrahydro-3-methoxy-12-methyl-5,7-dioxo-5H-indolo[2,3-a]pyrrolo[3,4-c]-carbazole; dark yellow amorphous powder which decomposes from about 240° C. (prepared from Example 1).

4b) 13-(3-aminopropyl)-3-chloro-6,7,12,13-tetrahydro-9-methoxy-12-methyl-5,7-dioxo-5H-indolo[2,3-a]pyrrolo-[3,4-c]carbazole; yellow amorphous powder; m.p. 276–281° C. (prepared from Example 1n).

In the case of the hydrogenation of Example 1a in methanol/ammonia/tetrahydrofuran in the presence of acetone under the conditions of Example 4, there is obtained the following compound:

4c) 13-(3-isopropylaminopropyl)-6,7,12,13-tetrahydro-13-methyl-5,7-dioxo-5H-indolo[2,3-a]pyrrolo[3,4-c]-carbazole; yellow amorphous powder; m.p. 205–210° C.

EXAMPLE 5

12-(2-Carbamoylethyl)-6,7,12,13-tetrahydro-5,7-dioxo-5H-indolo[2,3-a]pyrrolo[3,4-c]carbazole a) 740 mg (1.86 mmol) 12-(2-Carboxyethyl)-6,7,12,13-tetrahydro-5,7-dioxoindolo[2,3-a]furano[3,4-c]-carbazole are heated in an autoclave for 12 hours to 140° C. with 100 ml ammonia-saturated ethanol. After evaporation, the residue obtained is chromatographed on silica gel with toluene/tetrahydrofuran (4:1 v/v) and the fraction with the Rf 0.4 is isolated.

12-(2-carbamoylethyl)-6,7,12,13-tetrahydro-5,7-dioxo-5H-indolo[2,3-a]pyrrolo[3,4-c]carbazole is obtained in the form of dark yellow crystals which decompose from 310° C. The 12-(2-carboxyethyl)-6,7,12,13-tetrahydro-5,7- dioxoindolo[2,3-a]furano[3,4-c]carbazole used as starting material is prepared as follows: 980 mg (2.39 mmol) 12-(2-Carbamoylethyl)-6,7,12,13-tetrahydro-6-methyl-5,7-dioxo-5H-indolo[2,3-a]pyrrolo-[3,4-c]carbazole are heated under reflux for 1.5 hours in 200 ml 15% methanolic potassium hydroxide solution. After cooling, the reaction mixture is filtered, the filtrate is acidified with 2N hydrochloric acid and the product which precipitates out is filtered off and washed with water.

12-(2-Carboxyethyl)-6,7,12,13-tetrahydro-5,7-dioxoindolo[2,3-a]furano[3,4-c]carbazole is obtained as a brownish amorphous powder.

The 12-(2-carbamoylethyl)-6,7,12,13-tetrahydro-6-methyl-5,7-dioxo-5H-indolo[2,3-a]pyrrolo[3,4-c]-carbazole used as starting material is prepared as follows:

500 mg (1.47 mmol) 6,7,12,13-tetrahydro-6-methyl-5,7-dioxo-5H-indolo[2,3-a]pyrrolo[3,4-c]carbazole in 50 ml acetonitrile are stirred for 4 days at 20° C. with 1.05 g (14.8 mmol) acrylamide and 0.1 ml DBU. The suspension is evaporated, stirred with 30 ml dichloromethane/methanol (95:5 v/v) and the undissolved crystals are filtered off. 12-(2-carbamoylethyl)-6,7,12,13-tetrahydro-6-methyl-5,7-dioxo-5H-indolo[2,3-a]pyrrolo-[3,4-c]carbazole is obtained in the form of yellow crystals.

The 6,7,12,13-tetrahydro-6-methyl-5,1-dioxo-5H-indolo[2,3-a]pyrrolo[3,4-c]carbazole used as starting material is prepared as follows:

1 g (2.93 mmol) 3,4-bis-(indol-3-yl)-N-methyl-maleic acid imide is boiled under reflux for 1 hour with 800 mg (3.52 mmol) DDQ and 560 mg (2.94 mmol) p-toluenesulphonic acid hydrate in 200 ml toluene. Two thirds of the solvent are distilled off and the precipitate is filtered off and stirred with 100 ml 0.1N sodium hydroxide solution. It is filtered, the precipitate is washed with water, then suspended in ethanol and again filtered off.

6,7,12,13-Tetrahydro-6-methyl-5,7-dioxo-5H-indolo[2,3-a]pyrrolo[3,4-c]carbazole is obtained in the form of a yellow amorphous powder; m.p. >350° C.

The 3,4-bis-(indol-3-yl)-N-methylmaleic acid imide used as starting material is prepared in the manner described in the literature (see Tetrahedron, 1988, 44, 2887).

b) 12-(2-Carbamoylethyl)-6,7,12,13-tetrahydro-5,7-dioxo-5H-indolo[2,3-a]pyrrolo[3,4-c]carbazole (Example 5) can also be prepared from 12-(2-cyanoethyl)-6,7,12,13-tetrahydro-6-methyl-5,7-dioxo-5H-indolo-[2,3-a]pyrrolo[3,4-c]carbazole by reaction with methanolic potassium hydroxide solution and subsequent reaction with ammonia in ethanol in an autoclave in the manner described above in a). 12-(2-Cyanoethyl)-6,7,12,13-tetrahydro-6-methyl-5,7-dioxo-5H-indolo[2,3-a]pyrrolo[3,4-c]carbazole is prepared by the reaction of 6,7,12,13-tetrahydro-6-methyl-5,1-dioxo-5H-indolo[2,3-a]pyrrolo[3,4-c]-carbazole with acrylonitrile and DBU in acetonitrile in a manner analogous to the reaction with acrylamide described above in a).

EXAMPLE 6

(±)-12-(3-Diethylamino-2-hydroxy-1-propyl)-6,7,12,13-tetrahydro-5,7-dioxo-5H-indolo[2,3-a]pyrrolo[3,4-c]-carbazole 285 mg (0.63 mmol) (±)-12-(3-diethylamino-2-hydroxy-1-propyl)-6,7,12,13-tetrahydro-5,1-dioxoindolo-[2,3-a]furano[3,4-c]carbazole are heated in an autoclave for 6 hours at 140° C. in 30 ml of a saturated solution of ammonia in ethanol. The solution is evaporated, the residue is heated in 50 ml diisopropyl ether/tetrahydrofuran (4:1 v/v) and, after cooling, the crystals obtained are filtered off. (±)-12-(3-Diethylamino-2-hydroxy-1-propyl)-6,7,12,13-tetrahydro-5,1-dioxo-5H-indolo[2,3-a]pyrrolo[3,4-c]carbazole is obtained in the form of yellow crystals which decompose from 235° C.

The starting material is prepared in the following manner:

440 mg (0.94 mmol) (±)-12-(3-diethylamino-2-hydroxy-1-propyl)-6,7,12,13-tetrahydro-6-methyl-5,7-dioxo-5H-indolo[2,3-a]pyrrolo[3,4-c]carbazole are heated under reflux for 1.5 hours in 100 ml 10% methanolic potassium hydroxide solution. After cooling the reaction mixture is acidified with semi-concentrated hydrochloric acid, filtered and the filtrate evaporated. The residue is taken up in 10% potassium carbonate solution and ethyl acetate and the organic phase is washed with water and dried over anhydrous sodium sulphate. It is filtered, evaporated and the residue is stirred with 25 ml diisopropyl ether and the crystals formed are filtered off. (±)-12-(3-Diethylamino-2-hydroxy-1-propyl)-6,7,12,13-tetrahydro-5,7-dioxoindolo-[2,3-a]furano[3,4-c]carbazole is obtained in the form of yellow crystals which decompose from about 200° C.

The starting material is prepared in the following manner:

1 g (2.95 mmol) 6,7,12,13-Tetrahydro-6-methyl-5,7-dioxo-5H-indolo[2,3-a]pyrrolo[3,4-c]carbazole (precursor for Example 5) is dissolved in 15 ml dry dimethylformamide and added dropwise, under an atmosphere of argon, to a suspension of 100 mg (3.3 mmol) sodium hydride (80% in paraffin oil) in 25 ml dimethyl formamide. After stirring for 1 hour at 20° C., 915 mg (5.9 mmol) 1,1-diethyl-3-hydroxyazetidinium chloride are added thereto and the reaction mixture is stirred for 3 days at 20° C. The reaction mixture is evaporated in a vacuum, the residue is taken up in 150 ml of water and 500 ml ethyl acetate and the organic phase is separated off and dried over anhydrous sodium sulphate. After filtration, the filtrate is evaporated and the residue is chromatographed on silica gel with dichloromethane/methanol (99:1 v/v). The fraction with the Rf 0.2 in dichloromethane/methanol (95:5 v/v) is isolated, stirred with 20 ml diisopropyl ether and the crystals obtained are filtered off. (±)-12-(3-Diethylamino-2-hydroxy-1-propyl)-6,7,12,13-tetrahydro-6-methyl-5,7-dioxo-5H-indolo[2,3-a]pyrrolo[3,4-c]-carbazole is obtained in the form of yellow crystals; decomposition point 220–228° C.

EXAMPLE 7

12-(3-Dimethylaminopropyl)-6,7,12,13-tetrahydro-3,9-dimethoxy-5,7-dioxo-5H-indolo[2,3-a]pyrrolo[3,4-c]-carbazole 510 mg (1.08 mmol) 12-(3-Dimethylaminopropyl)-6,7,12,13-tetrahydro-3,9-dimethoxy-5,7-dioxoindolo-[2,3-a]furano[3.4-c]carbazole are heated in an autoclave for 24 hours at 140° C. in 40 ml of a saturated solution of ammonia in ethanol. After cooling, the precipitate obtained is filtered off with suction, chromatographed on silica gel with toluene/ethanol (10:1 v/v) and the fraction with the Rf 0.25 in toluene/ethanol (5:1 v/v) is isolated. 12-(3-Dimethylaminopropyl)-6,7,12, 13-tetrahydro-3,9-dimethoxy-5,7-dioxo-5H-indolo[2,3-a]-pyrrolo[3,4-c]carbazole is obtained in the form of yellow crystals which decompose from about 230° C. This compound can also be prepared from the same starting material by reaction with hexamethyldisilazane and methanol in dimethylformamide analogously to the process described in the literature (Tetrahedron Lett., 1990, 31, 5201).

The starting material is prepared from 12-(3-dimethylaminopropyl)-6,7,12,13-tetrahydro-3,9-dimethoxy-6-methyl-5,-dioxo-5H-indolo[2,3-a]pyrrolo[3,4-c]-carbazole by reaction with methanolic potassium hydroxide solution in a manner analogous to that described for the corresponding precursor of Example 6.

12-(3-Dimethylaminopropyl)-6,7,12,13-tetrahydro-3,9-dimethoxy-6-methyl-5,7-dioxo-5H-indolo[2,3-a]pyrrolo-[3,4-c]carbazole is prepared in the following manner:

A solution of 2.0 g (5 mmol) 6,7,12,13-tetrahydro-3,9-dimethoxy-6-methyl-5,7-dioxo-5H-indolo[2,3-a]-pyrrolo[3,4-c]carbazole in 100 ml dry dimethylformamide is added dropwise at 20° C. to a suspension of 182 mg (6.1 mmol) sodium hydride (80% in paraffin oil) in 5 ml dimethylformamide. After stirring for 1 hour at 20° C. 738 mg (6.1 mmol) 3-dimethylaminopropyl chloride are added thereto and the reaction mixture is stirred for 20 hours at 20° C. The solvent is distilled off in a vacuum, the residue is mixed with 150 ml ethyl acetate and 150 ml of water and the solid material insoluble in both phases is filtered off. The solid material is taken up in tetrahydrofuran, the tetrahydrofuran solution is washed with a saturated sodium chloride solution, dried over anhydrous sodium sulphate, filtered and evaporated. The residue, together with the residue from the ethyl acetate solution, is chromatographed on silica gel with ethyl acetate/methanol (4:1 v/v). The fraction with the Rf 0.2 in ethyl acetate/methanol (3:1 v/v) is isolated and stirred with diisopropyl ether/ethyl acetate (9:1 v/v). The crystals formed are filtered off. 12-(3-Dimethylaminopropyl)-6,7,12,13-tetrahydro-3,9-dimethoxy-6-methyl-5,7-dioxo-5H-indolo-[2,3-a]pyrrolo[3,4-c]carbazole is obtained in the form of yellow-brown crystals.

6,7,12,13-Tetrahydro-3,9-dimethoxy-6-methyl-5,7-dioxo-5H-indolo[2,3-a]pyrrolo[3,4-c]carbazole is prepared by the oxidative cyclisation of 3,4-bis-(5-methoxyindol-3-yl)-N-methylmaleic acid imide (prepared analogously to Tetrahedron, 1988, 44, 2887) with DDQ and p-toluenesulphonic acid hydrate in toluene in a manner analogous to that described in Example 5 for 3,4-bis-(indol-3-yl)-N-methylmaleic acid imide.

The following compounds are prepared in an analogous manner:

7a) 13-(3-dimethylaminopropyl)-6,7,12,13-tetrahydro-5,7-dioxo-5H-indolo[2,3-a]pyrrolo[3,4-c]carbazole; bright yellow crystals which decompose from 288° C.

7b) 6,7,12,13-tetrahydro-3,9-dimethoxy-12-methyl-5,7-dioxo-5H-indolo[2,3-a]pyrrolo[3,4-c]carbazole; yellow crystals; m.p. >330° C. The 6,7,12,13-tetrahydro-3,9-dimethoxy-6,12-dimethyl-5,1-dioxo-5H-indolo[2,3-a] pyrrolo[3,4-c]-carbazole used as starting material is prepared by the methylation of 6,7,12,13-tetrahydro-3,9-dimethoxy-6-methyl-5,7-dioxo-5H-indolo[2,3-a]pyrrolo [3,4-c]-carbazole (precursor for Example 7) with methyl iodide or dimethyl sulphate in the following manner:

A solution of 1 g (2.5 mmol) 6,7,12,13-tetrahydro-3,9-dimethoxy-6-methyl-5,7-dioxo-5H-indolo[2,3-a]-pyrrolo[3,4-c]carbazole in 50 ml dry dimethylformamide is added dropwise at 20° C. to a suspension of 91 mg (3.0 mmol) sodium hydride (80% in paraffin oil) in 5 ml dimethylformamide under an atmosphere of argon. After stirring for 1 hour at 20° C., 0.2 ml (3.2 mmol) methyl iodide are added thereto and the reaction mixture is stirred for 16 hours at 20° C. It is then evaporated in a vacuum and the residue is partitioned between ethyl acetate and water. The ethyl acetate phase is separated off, dried over anhydrous sodium sulphate, filtered and evaporated. The residue is stirred with 30 ml diisopropyl ether/ethyl acetate (2:1 v/v) and the undissolved product is filtered off. 6,7,12,13-Tetrahydro-3,9-dimethoxy-6,12-dimethyl-5,7-dioxo-5H-indolo[2,3-a]-pyrrolo[3,4-c]carbazole is obtained in the form of a pale brown amorphous powder.

The methylation can also be carried out in an analogous manner with dimethyl sulphate as alkylation agent.

7c) 6,7,12,13-tetrahydro-12-methyl-5,7-dioxo-5H-indolo[2,3-a]pyrrolo[3,4-c]carbazole; yellow crystals; m.p. >340° C.

7d) 6,7,12,13-tetrahydro-3-methoxy-12-methyl-5,7-dioxo-5H-indolo[2,3-a]pyrrolo[3,4-c]carbazole; orange-coloured crystals which decompose from about 335° C.

7e) 6,7,12,13-tetrahydro-12,13-dimethyl-5,7-dioxo-5H-indolo[2,3-a]pyrrolo[3,4-c]carbazole; yellow crystals; m.p. >330° C. The 6,7,12,13-tetrahydro-6,12,13-trimethyl-5,7-dioxo-5H-indolo[2,3-a]pyrrolo[3,4-c] carbazole (yellow crystals which decompose from 305° C.) used as starting material is prepared by the dimethylation of 6,7,12,13-tetrahydro-6-methyl-5,7-dioxo-5H-indolo[2,3-a]pyrrolo-[3,4-c]carbazole (precursor for Example 5) with two equivalents of sodium hydride and two equivalents of methylation agent in the manner described in Example 7b or by the trimethylation of the known 6,7,12,13-tetrahydro-5,1-dioxo-5H-indolo[2,3-a] pyrrolo[3,4-c]carbazole (Example 11a) with three equivalents of sodium hydride and three equivalents of methylation agent, again in a manner analogous to that described in Example 7b.

7f) 6,7,12,13-tetrahydro-12,13-diethyl-5,7-dioxo-5H-indolo [2,3-a]pyrrolo[3,4-c]carbazole; bright yellow crystals; m.p. 370° C. The preparation is analogous to Example 7e, using ethyl bromide as alkylation agent.

7g) 12-(3-diisopropylaminopropyl)-6,7,12,13-tetrahydro-5,7-dioxo-5H-indolo[2,3-a]pyrrolo[3,4-c]carbazole; yellow amorphous powder; m.p. 225–221° C.

7h) 12-(3-diisopropylaminopropyl)-6,7,12,13-tetrahydro-13-methyl-5,7-dioxo-5H-indolo[2,3-a]pyrrolo[3,4-c]-carbazole; yellow crystals; m.p. 268–270° C. This compound is prepared analogously to Example 1, starting from 6,7,12,13-tetrahydro-6,12-dimethyl-5,1-dioxo-5H-indolo[2,3-a]pyrrolo[3,4-c]carbazole. The precursor is prepared by oxidative cyclisation of 3-(1-methyl-3-indolyl)-4-(3-indolyl)-N-methylmaleic acid imide with DDQ and p-toluene sulphonic acid hydrate in toluene in a manner analogous to that described in Example 5 for 3,4-bis-(indol-3-yl)-N-methylmaleic acid imide.

7i) 6,7,12,13-tetrahydro-5,7-dioxo-3,9-di-n-propoxy-5H-indolo[2,3-a]pyrrolo[3,4-c]carbazole; orange-coloured crystals; m.p. >350° C. The compound is prepared analogously to Example 7 starting from 6,7,12,13-tetrahydro-6-methyl-5,7-dioxo-3,9-di-n-10 propoxy-5H-indolo[2,3-a]pyrrolo[3,4-c]carbazole. The precursor is prepared by the oxidative cyclisation of 3-(5-n-propoxy-3-indolyl)-4-(5-n-propoxy-3-indolyl)-N-methylmaleic acid imide with DDQ and p-toluene-sulphonic acid hydrate in toluene in a manner analogous to that described in Example 5 for 3,4-bis-(indol-3-yl)-N-methylmaleic acid imide. 3-(5-n-propoxy-3-indolyl)-4-(5-n-propoxy-3-indolyl)-N-methylmaleic acid imide is prepared analogously to the literature (Tetrahedron, 1988, 44, 2887) from 3,4-dibromo-N-methylmaleic acid imide and 5-n-propoxyindole.

EXAMPLE 8

12-(2,3-Dihydroxy-1-propyl)-6,7,12,13-tetrahydro-5,7-dioxo-5H-indolo[2,3-a]pyrrolo[3,4-c]carbazole 150 mg (0.34 mmol) 12-(2,2-dimethyl-1,3-dioxolan-4-ylmethyl)-6,7,12,13-tetrahydro-5,7-dioxo-5H-indolo-[2,3-a]pyrrolo[3,4-c]carbazole in 50 ml 1N hydrochloric acid/ethanol (1:1 v/v) are stirred for 16 hours at 60° C. After cooling, the reaction mixture is neutralised with 10% potassium hydrogen carbonate solution and extracted twice with, in each case, 100 ml ethyl acetate. The ethyl acetate extracts are washed with 100 ml of water, dried over anhydrous sodium sulphate, filtered and evaporated. The residue is chromatographed on silica gel with toluene/acetone (4:1 v/v) and the fraction with the Rf 0.2 in toluene/acetone (3:1 v/v)

is isolated. 12-(2,3-Dihydroxy-1-propyl)-6,7,12,13-tetrahydro-5,7-dioxo-5H-indolo[2,3-a]pyrrolo[3,4-c] carbazole is obtained in the form of an orange amorphous powder which decomposes from about 310° C.

The starting material is prepared from 12-(2,2-dimethyl-1,3-dioxolan-4-ylmethyl)-6,7,12,13-tetrahydro-6-methyl-5,7-dioxo-5H-indolo[2,3-a]pyrrolo[3,4-c]-carbazole by reaction with 15% methanolic potassium hydroxide solution by heating under reflux for 16 hours analogously to Example 6 to give 12-(2,2-dimethyl-1,3-dioxolan-4-ylmethyl)-6,7,12,13-tetrahydro-5,1-dioxo-5H-indolo[2,3-a]pyrrolo[3,4-c] carbazole and subsequent reaction with hexamethyldisilazane and methanol in dimethylformamide analogously to Tetrahedron Lett. 1990, 5201.

12-(2,2-Dimethyl-1,3-dioxolan-4-ylmethyl)-6,7,12,13-tetrahydro-6-methyl-5,7-dioxo-5H-indolo-[2,3-a]pyrrolo[3,4-c]carbazole is prepared in the following manner:

3 g (8.84 mmol) 6,7,12,13-Tetrahydro-6-methyl-5,1-dioxo-5H-indolo[2,3-a]pyrrolo[3,4-c]carbazole (precursor for Example 5) are stirred for 2 hours at 20° C. with 595 mg (9 mmol) powdered potassium hydroxide, 620 mg (4.5 mmol) potassium carbonate and 300 mg (1.1 mmol) 18-crown-6 in 200 ml toluene under an atmosphere of nitrogen. Subsequently, 2.6 g (9 mmol) 2,2-dimethyl-4-(4-methylphenylsulphonyloxymethyl)-1,3-dioxolan (see Biochemistry, 1971, 10, 3204) are added thereto and the reaction mixture is heated under reflux for 16 hours. After cooling, the reaction mixture is evaporated in a vacuum and the residue is taken up in ethyl acetate and water. The ethyl acetate solution is separated off, washed with water, dried over anhydrous sodium sulphate, filtered and evaporated. The residue is chromatographed on silica gel with toluene/acetone (9:1 v/v), the fraction with the Rf 0.65 in toluene/acetone (3:1 v/v) is isolated, stirred with 20 ml diisopropyl ether/acetone (4:1 v/v) and the yellow crystals formed of 12-(2,2-dimethyl-1,3-dioxolan-4-ylmethyl)-6,7,12,13-tetrahydro-6-methyl-5,7-dioxo-5H-indolo[2,3-a]pyrrolo-[3,4-c]carbazole filtered off.

EXAMPLE 9

12-(4-Aminobutyl)-6,7,12,13-tetrahydro-13-methyl-5,7-dioxo-5H-indolo[2,3-a]pyrrolo[3,4-c]carbazole 300 mg (0.1 mmol) 12-(4-Azidobutyl)-6,7,12,13-tetrahydro-13-methyl-5,7-dioxo-5H-indolo[2,3-a]-pyrrolo[3,4-c]carbazole (see Example 1w) in 40 ml tetrahydrofuran/ethanol (1:1 v/v) are hydrogenated in the presence of 300 mg 5% palladium on active carbon at 25° C. and 50 bar pressure for 48 hours in an autoclave. After filtration of the solution, the solvent is distilled off and the residue is crystallised from ethanol. 12-(4-Aminobutyl)-6,7,12,13-tetrahydro-13-methyl-5,7-dioxo-5H-indolo[2,3-a]pyrrolo[3,4-c]carbazole is obtained in the form of yellow crystals; m.p.10 220–223° C.

The following compound is obtained in an analogous manner:

9a) 12-(5-aminopentyl)-6,7,12,13-tetrahydro-13-methyl-5,7-dioxo-5H-indolo[2,3-a]pyrrolo[3,4-c]carbazole; yellow crystals; m.p. 177–181° C., prepared from Example 1w.

EXAMPLE 10

(±)-12-(3-Dimethylamino-2-hydroxy-1-propyl)-6,7,12,13-tetrahydro-13-methyl-5,7-dioxo-5H-indolo[2,3-a]pyrrolo-[3,4-c]carbazole 750 mg (1.7 mmol) (±)-12-(3-Dimethylamino-2-hydroxy-1-propyl)-6,7,12,13-tetrahydro-13-methyl-5,7-dioxoindolo[2,3-a]furano[3,4-c]carbazole are heated in an autoclave with 50 ml ammonia-saturated ethanol for 20 hours at 140° C. The undissolved product is filtered off and again crystallised from ethanol. (±)-12-(3-Dimethylamino-2-hydroxy-1-propyl)-6,7,12,13-tetrahydro-13-methyl-5,7-dioxo-5H-indolo[2,3-a]-pyrrolo[3,4-c]carbazole is obtained in the form of a yellow amorphous powder; m.p. 260–270° C.

The starting material is prepared in the following manner:

950 mg (2.1 mmol) (±)-12-(3-dimethylamino-2-hydroxy-1-propyl)-6,7,12,13-tetrahydro-6,13-dimethyl-5,7-dioxo-5H-indolo[2,3-a]pyrrolo[3,4-c]carbazole are heated under reflux for 16 hours in 150 ml 15% methanolic potassium hydroxide solution. The solution is evaporated to one half, mixed with 100 ml of water and weakly acidified with semi-concentrated hydrochloric acid. The precipitate obtained is filtered off, stirred with 50 ml 5% sodium hydrogen carbonate solution, again filtered and dried. (±)-12-(3-Dimethylamino-2-hydroxy-1-propyl)-6,7,12,13-tetrahydro-13-methyl-5,7-dioxo-indolo[2,3-a]furano[3,4-c]carbazole is obtained in the form of a yellow amorphous powder.

The starting material is prepared in the following manner:

950 mg (2.3 mmol) (±)-12-epoxymethyl-6,7,12,13-tetrahydro-6,13-dimethyl-5,7-dioxo-5H-indolo[2,3-a]-pyrrolo[3,4-c]carbazole are heated for 2 hours at 50° C. in 150 ml of a 33% solution of dimethylamine in ethanol. After cooling, the solution is evaporated, the residue is stirred with 25 ml diisopropyl ether/acetone (4:1 v/v) and the product is filtered off. (±)-12-(3-Dimethylamino-2-hydroxy-1-propyl)-6,7,12,13-tetrahydro-6,13-dimethyl-5,7-dioxo-5H-indolo[2,3-a]-pyrrolo[3,4-c]carbazole is obtained in the form of a yellow powder; m.p. 198–203 ° C.

The starting material is prepared in the following manner:

3.9 g (9.5 mmol) (±)-3-(1-Epoxymethyl-3-indolyl)-4-(1-methyl-3-indolyl)-N-methylmaleimide, 2.16 g (11.4 mmol) p-toluene-sulphonic acid hydrate and 4.2 g (19 mmol) DDQ are heated under reflux for 15 hours in 1.5 l of toluene. The reaction mixture is evaporated in a vacuum, the residue is treated with 300 ml 1N aqueous sodium hydroxide solution in an ultrasonic bath, extracted with a saturated solution of sodium chloride and twice with, in each case, 300 ml tetrahydrofuran. The tetrahydrofuran solution is washed twice with, in each case, 300 ml of saturated sodium chloride solution, dried over anhydrous sodium sulphate and evaporated. The residue is chromatographed on silica gel with dichloromethane as elution agent. The fraction with the Rf 0.1 in toluene/acetone (3:1 v/v) is isolated, stirred with 20 ml diisopropyl ether/acetone (4:1 v/v) and the undissolved product is filtered off. (±)-12-Epoxymethyl-6,7,12,13-tetrahydro-6,13-dimethyl-5,7-dioxo-5H-indolo[2,3-a] pyrrolo[3,4-C]-carbazole is obtained in the form of a yellow amorphous powder. The starting material is prepared in the following manner: 4.0 g (11.2 mmol) 3-(1-Methyl-3-indolyl)-4-(3-indolyl)-N-methylmaleic acid imide in 100 ml dry dimethylformamide is mixed portionwise under an atmosphere of nitrogen at 0° C. with 405 mg (13.5 mmol) sodium hydride (80% in mineral oil). After stirring for 1 hour at 0° C., 3.1 g (22.6 mmol) epibromohydrin in 10 ml dimethylformamide are added dropwise thereto and the reaction mixture subsequently stirred for 16 hours at 20° C. The solution is mixed with 400 ml of a saturated solution of sodium chloride and 400 ml tetrahydrofuran, the organic phase is separated off and the aqueous phase is again extracted with 400 ml tetrahydrofuran. The organic phases are washed twice with, in each case, 400 ml of a saturated solution of sodium chloride, dried over anhydrous sodium sulphate, filtered and evaporated. The residue is chromatographed on silica gel with dichloromethane. The fraction with the Rf 0.6 in toluene/acetone (3:1 v/v) is isolated. (±)-3-(1-Epoxymethyl-3-indolyl)-4-(1-methyl-3-indolyl)-

N-methylmaleic acid imide is obtained in the form of a red amorphous substance. The starting material is prepared by the reaction of 3-bromo-4-(1-methyl-3-indolyl)-N-methylmaleic acid imide with indolyl magnesium bromide analogously to the literature (see Tetrahedron, 1988, 44, 2887).

3-Bromo-4-(1-methyl-3-indolyl)-N-methylmaleic acid imide is prepared as follows:

15 g (49.2 mmol) 3-Bromo-4-(3-indolyl)-N-methylmaleic acid imide (see Tetrahedron, 1988, 44, 2887) in 330 ml dry tetrahydrofuran are mixed portionwise, under an atmosphere of nitrogen, at 4° C. with 1.5 g (50 mmol) sodium hydride (80% in mineral oil). After stirring for 1 hour at 4° C., 7.5 g (53 mmol) methyl iodide in 35 ml tetrahydrofuran are added dropwise thereto and the reaction mixture is subsequently stirred for 15 hours at 20° C. The solution is washed twice with, in each case, 300 ml of a solution of sodium chloride, dried over anhydrous sodium sulphate, filtered and evaporated. The residue is crystallised from 100 ml methanol. 3-Bromo-4-(1-methyl-3-indolyl)-N-methylmaleic acid imide is obtained in the form of an orange-coloured powder.

The following compounds are obtained in an analogous manner:

10a) (±)-12-(3-diethylamino-2-hydroxy-1-propyl)-6,7,12,13-tetrahydro-13-methyl-5,7-dioxo-5H-indolo-[2,3-a]pyrrolo[3,4-c]carbazole; yellow amorphous powder; soften from about 185 to 260° C.

10b) (±)-13-(3-dimethylamino-2-hydroxy-1-propyl)-6,7,12,13-tetrahydro-3-methoxy-12-methyl-5,7-dioxo-5H-indolo[2,3-a]pyrrolo[3,4-c]carbazole; yellow amorphous powder; m.p. 235–240° C.

10c) (±)-12-(3-dimethylamino-2-hydroxy-1-propyl)-6,7,12,13-tetrahydro-3-methoxy-13-methyl-5,7-dioxo-5H-indolo[2,3-a]pyrrolo[3,4-c]carbazole; yellow amorphous powder; m.p. 240–250° C.

10d) (±)-12-(3-diisopropylamino-2-hydroxy-1-propyl)-6,7,12,13-tetrahydro-13-methyl-5,7-dioxo-5H-indolo-[2,3-a]pyrrolo[3,4-c]carbazole; yellow amorphous powder; m.p. 256–260° C.

10e) (±)-12-(3-pyrrolidino-2-hydroxy-1-propyl)-6,7,12,13-tetrahydro-13-methyl-5,7-dioxo-5H-indolo-[2,3-a]pyrrolo[3,4-c]carbazole; yellow amorphous powder; m.p. 130–135° C.

EXAMPLE 11

For the following known indolocarbazole derivatives of general formula Ia unsubstituted on the indole nitrogen atom (Examples 11a–11h), prepared according to processes known from the literature or analogously to processes known from the literature, there was, surprisingly, also found inhibitory actions for protein kinases and especially for protein kinase C and/or myosin light-chain kinase:

11a) 6,7,12,13-tetrahydro-5,7-dioxo-5H-indolo[2,3-a]pyrrolo[3,4-c]carbazole; yellow crystals; m.p. >370° C.

11b) 6,7,12,13-tetrahydro-3-methoxy-5,7-dioxo-5H-indolo[2,3-a]pyrrolo[3,4-c]carbazole; dark yellow crystals; m.p. >330° C.

11c) 2-chloro-6,7,12,13-tetrahydro-5,7-dioxo-5H-indolo[2,3-a]pyrrolo[3,4-c]carbazole; bright yellow crystals; m.p. >350° C.

11d) 6,7,12,13-tetrahydro-3,9-dimethoxy-5,7-dioxo-5H-indolo[2,3-a]pyrrolo[3,4-c]carbazole; yellow crystals; m.p. >300° C.

11e) 6,7,12,13-tetrahydro-3,9-dimethyl-5,7-dioxo-5H-indolo[2,3-a]pyrrolo[3,4-c]carbazole; orange crystals; m.p. >300° C.

11f) 3,9-dichloro-6,7,12,13-tetrahydro-5,7-dioxo-5H-indolo[2,3-a]pyrrolo[3,4-c]carbazole; yellow crystals; m.p. >300° C.

11g) 3,9-dibromo-6,7,12,13-tetrahydro-5,7-dioxo-5H-indolo[2,3-a]pyrrolo[3,4-c]carbazole; yellow crystals; m.p. >300° C.

11h) 1,11-dichloro-6,7,12,13-tetrahydro-5,7-dioxo-5H-indolo[2,3-a]pyrrolo[3,4-c]carbazole; dark yellow crystals; m.p. >340° C.

We claim:

1. A method of inhibiting myosin light chain kinase in a mammal in need thereof comprising administering to the mammal an effective amount of an indolocarbazole imide of the general formula (I)

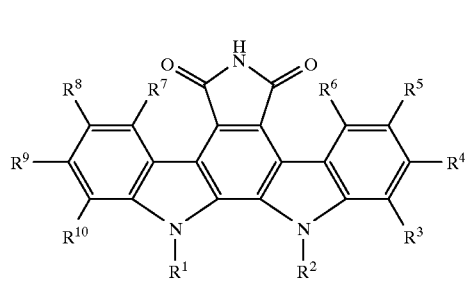

wherein $R^1$ and $R^2$ are the same or different and, in each case, are a hydrogen atom, a straight-chained or branched alkyl, radical containing up to 6 carbon atoms, or alkenyl radical or alkynyl radical of from 2 to 6 carbon atoms, an epoxyalkyl radical containing up to 4 carbon atoms, an unsubstituted or substituted phenyl or phenylalkyl radical containing, in each case, up to 12 carbon atoms, a cyano group, a straight-chained or branched cyanoalkyl, cyanoalkenyl, cyanoalkynyl, dicyanoalkyl, dicyanoalkenyl, azidoalkyl, azidoalkenyl, haloalkyl, di- or trihaloalkyl, halohydroxyalkyl, hydroxyalkyl, acyloxyalkyl, dihydroxyalkyl, alkoxyalkyl, alkylthioalkyl, alkylsulphinylalkyl, alkylsulphonylalkyl, cyanoalkoxyalkyl, cyanoalkylthioalkyl, isocyanoalkyl, carboxyalkyl, amidinoalkyl, amidinothioalkyl, (2-nitroguanidino)alkyl, cyanatoalkyl, isocyanatoalkyl, thiocyanatoalkyl or isothiocyanatoalkyl radical containing, in each case, up to 6 carbon atoms, a phenylsulphonyloxyalkyl or alkylsulphonyloxyalkyl radical containing up to 12 carbon atoms, a straight-chained or branched aminoalkyl radical containing up to 12 carbon atoms unsubstituted on the nitrogen atom or mono-, di- or trisubstituted by benzyl radicals or alkyl radicals containing up to 4 carbon atoms or in which two substituents on the nitrogen atom, together with the nitrogen atom or a substituent on the nitrogen atom and a substituent of the alkyl chain and together with the nitrogen atom form a heterocyclic ring containing 3 to 6 carbon atoms, which optionally contains oxygen, sulphur and/or further nitrogen atoms and optionally is substituted by an alkyl radical containing up to 4 carbon atoms, whereby the alkyl chain optionally is substituted further by $C_1$–$C_4$-alkyl radicals, a hydroxyl group or a $C_1$–$C_4$-alkoxy radical, an acylaminoalkyl radical containing up to 6 carbon atoms, an alkoxycarbonylalkyl radical containing up to 7 carbon atoms, a radical of the general formula:

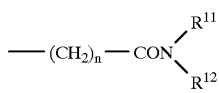

in which n is 1, 2 or 3 and $R^{11}$ and $R^{12}$ are the same or different and, in each case, stand for a hydrogen atom or an alkyl radical containing up to 6 carbon atoms or an acyl radical containing up to 4 carbon atoms or $R^1$ and $R^2$ together signify an alkylene radical containing 2 to 4 carbon atoms, which is optionally substituted by a hydroxyl group, an alkoxy radical containing up to 4 carbon atoms or an amino group unsubstituted or mono- or disubstituted by benzyl radicals or alkyl radicals containing up to 4 carbon atoms and $R^3$ to $R^{10}$, independently of one another, are each a hydrogen atom, a $C_1$–$C_4$-alkyl, $C_1$–$C_4$-alkoxy, $C_1$–$C_4$-alkylthio, benzyloxy, $C_1$–$C_4$-acyl, halogen, nitro, hydroxyl, acyloxy, trifluoromethyl, amino, unsubstituted or mono- or disubstituted by benzyl radicals or alkyl radicals containing up to 4 carbon atoms, aminoalkyl or aminoalkoxy containing up to 12 carbon atoms, unsubstituted on the nitrogen atom or mono- or disubstituted by benzyl radicals or alkyl radicals containing up to 4 carbon atoms, hydroxyalkyl containing up to 4 carbon atoms, carboxyl, acylamino containing up to 4 carbon atoms, haloalkyl containing up to 4 carbon atoms, $C_1$–$C_4$-alkylsulphinyl or alkylsulphonyl, sulpho, carbamoyl, mono- or di-($C_1$–$C_4$-alkyl)carbamoyl or cyano or two neighboring substituents together stand for a methylenedioxy radical, with the proviso that, if $R^3$ and $R^{10}$ simultaneously stand for hydroxyl groups, not all of the other symbols $R^1$ to $R^{10}$ stand for hydrogen atoms, with the proviso that: (1) not all of the symbols $R^1$ to $R^{10}$ simultaneously stand for hydrogen atoms and that (2) all the other symbols do not simultaneously stand for hydrogen atoms when (a) $R^1$ is a 3-dimethylaminopropyl radical or when (b) $R^3$ and $R^{10}$ simultaneously stand for chlorine, hydroxyl or methoxy or when (c) $R^4$ and/or $R^9$ stand for chlorine, hydroxyl or methoxy or when (d) $R^5$ and/or $R^8$ stand for methyl, methoxy, benzyloxy, nitro, chlorine, bromine or fluorine;
or the pharmacologically acceptable salt thereof.

2. The method of claim 1, wherein $R^1$ and $R^2$ are the same or different and, in each case, stand for hydrogen, methyl, ethyl, cyanomethyl, 2-cyanoethyl, 3-cyanopropyl, 3-cyano-2-propyl, 2-azidoethyl, 3-azido-propyl, 2,3-dihydroxypropyl, 3-chloro-2-hydroxy-1-propyl, 3-aminopropyl, 3-dimethylaminopropyl, 3-trimethylammoniopropyl, 4-aminobutyl, 5-aminopentyl, epoxymethyl, 2-epoxyethyl, 3-methylaminopropyl, 3-ethylaminopropyl, 3-isopropylaminopropyl, 3-diisopropylaminopropyl, 3-methylamino-2-hydroxy-1-propyl, 3-ethylamino-2-hydroxy-1-propyl, 3-isopropylamino-2-hydroxy-1-propyl, 3-dimethylamino-2-hydroxy-1-propyl, 3-diethylamino-2-hydroxy-1-propyl, 3-diisopropylamino-2-hydroxy-1-propyl, 3-pyrrolidino-2-hydroxy-1-propyl or the radical —$(CH_2)_2CONH_2$ and $R^3$ to $R^{10}$, independently of one another, stand for hydrogen, methyl, methoxy, n-propoxy, chlorine, bromine, nitro, hydroxyl or amino or two neighbouring radicals together stand for a methylenedioxy radical.

3. The method of claim 1, wherein $R^1$ or $R^2$ is independently cyanoalkyl.

4. The method of claim 1, wherein $R^8$ is alkoxy.

5. The method of the claim 4, wherein $R^2$ is alkyl.

6. The method of claim 1, wherein $R^2$ or $R^3$ independently is dialkylaminoalkyl.

7. The method of claim 1, wherein $R^5$ is alkoxy.

8. The method of claim 7, wherein $R^1$ or $R^2$ independently is alkyl.

9. The method of claim 1, wherein $R^1$ or $R^2$ independently is azidoalkyl.

10. The method of claim 1, wherein $R^1$ or $R^2$ independently is epoxyalkyl.

11. The method of claim 1, wherein $R^1$ or $R^2$ independently is hydroxyalkyl.

12. The method of claim 1, wherein $R^1$ or $R^2$ independently is dihydroxyalkyl.

13. The method of claim 1, wherein $R^1$ or $R^2$ independently is aminoalkyl.

14. The method of claim 1, wherein $R^1$ or $R^2$ independently is dialkylaminoalkyl.

15. The method of claim 1, wherein $R^3$–$R^{10}$ are arranged so that two neighboring substituents together stand for methylenedioxy radical.

16. The method of claim 1, wherein $R^9$ or $R^{10}$ independently is alkoxy.

17. The method of claim 1, wherein $R^8$, $R^9$, $R^4$ or $R^5$ independently is alkoxy.

18. The method of claim 1, wherein $R^1$ or $R^2$ independently is carbamoylalkyl.

19. The method of claim 1, wherein $R^1$ and/or $R^2$ independently has a heterocyclic ring.

20. The method of claim 19 wherein the ring is a pyrrolo ring.

21. The method of claim 1 wherein the indolocarbazole imide of Formula I is:
13-(2-cyanoethyl)-6,7,12,13-tetrahydro-3-methoxy-12-methyl-5,7-dioxo-5H-indolo[2,3-a]pyrrolo[3,4-c]carbazole;
12-(2-cyanoethyl)-6,7,12,13-tetrahydro-13-methyl-5,7-dioxo-5H-indolo[2,3-a]pyrrolo[3,4-c]carbazole;
12-(2-cyanoethyl)-6,7,12,13-tetrahydro-3-methoxy-13-methyl-5,7-dioxo-5H-indolo[2,3-a]pyrrolo[3,4-c]carbazole;
12-(2-cyanoethyl)-6,7,12,13-tetrahydro-3,9-dimethoxy-13-methyl-5,7-dioxo-5H-indolo[2,3-a]pyrrolo[3,4-c]carbazole;
12-(3-cyano-2-propyl)-6,7,12,13-tetrahydro-13-methyl-5,7-dioxo-5H-indolo[2,3-a]pyrrolo[3,4-c]carbazole;
12-cyanomethyl-6,7,12,13-tetrahydro-13-methyl-5,7-dioxo-5H-indolo[2,3-a]pyrrolo[3,4-c]carbazole;
3-chloro-13-(2-cyanoethyl)-6,7,12,13-tetrahydro-12-methyl-5,7-dioxo-5H-indolo[2,3-a]pyrrolo[3,4-c]carbazole;
12-(3-cyanopropyl)-6,7,12,13-tetrahydro-13-methyl-5,7-dioxo-5H-indolo[2,3-a]pyrrolo[3,4-c]carbazole;
12-(3-cyanopropyl)-6,7,12,13-tetrahydro-3-methoxy-13-methyl-5,7-dioxo-5H-indolo[2,3-a]pyrrolo[3,4-c]carbazole;
13-(2-cyanoethyl)-6,7,12,13-tetrahydro-2,3-dimethoxy-12-methyl-5,7-dioxo-5H-indolo[2,3-a]pyrrolo[3,4-c]carbazole;
13-(2-cyanoethyl)-6,7,12,13-tetrahydro-12-methyl-5,7-dioxo-3-n-propoxy-5H-indolo[2,3-a]pyrrolo[3,4-c]carbazole;
13-(3-cyanopropyl)-6,7,12,13-tetrahydro-3-methoxy-12-methyl-5,7-dioxo-5H-indolo[2,3-a]pyrrolo[3,4-c]carbazole;
12-(3-cyanopropyl)-6,7,12,13-tetrahydro-3,9-dimethoxy-13-methyl-5,7-dioxo-5H-indolo[2,3-a]pyrrolo[3,4-c]carbazole;
13-(2-cyanoethyl)-6,7,12,13-tetrahydro-2,3,9-trimethoxy-12-methyl-5,7-dioxo-5H-indolo[2,3-a]pyrrolo[3,4-c]carbazole;

13-(2-cyanoethyl)-6,7,12,13-tetrahydro-1-methoxy-12-methyl-5,7-dioxo-5H-indolo[2,3-a]pyrrolo[3,4-c]-carbazole;

13-(2-cyanoethyl)-6,7,12,13-tetrahydro-2-methoxy-12-methyl-5,7-dioxo-5H-indolo[2,3-a]pyrrolo[3,4-c]-carbazole;

12-(4-azidobutyl)-6,7,12,13-tetrahydro-13-methyl-5,7-dioxo-5H-indolo[2,3-a]pyrrolo[3,4-c]carbazole;

12-(5-azidopentyl)-6,7,12,13-tetrahydro-13-methyl-5,7-dioxo-5H-indolo[2,3-a]pyrrolo[3,4-c]carbazole;

12-epoxymethyl-6,7,12,13-tetrahydro-13-methyl-5,7-dioxo-5H-indolo[2,3-a]pyrrolo[3,4-c]carbazole; or (±)-12-(3-chloro-2-hydroxy-1-propyl)-6,7,12,13-10 tetrahydro-13-methyl-5,7-dioxo-5H-indolo[2,3-a]pyrrolo-[3,4-c]carbazole.

22. The method of claim 1 wherein the imide is:
13-(2-cyanoethyl)-6,7,12,13-tetrahydro-3-hydroxy-12-methyl-5,7-dioxo-5H-indolo[2,3-a]pyrrolo[3,4-c]-carbazole;

12-(2-cyanoethyl)-6,7,12,13-tetrahydro-3-hydroxy-13-methyl-5,7-dioxo-5H-indolo[2,3-a]pyrrolo[3,4-c]-carbazole;

13-(2-cyanoethyl)-6,7,12,13-tetrahydro-2,3-dihydroxy-12-methyl-5,7-dioxo-5H-indolo[2,3-a]pyrrolo[3,4-c]-carbazole;

12-(3-dimethylaminopropyl)-6,7,12,13-tetrahydro-3,9-dihydroxy-5,7-dioxo-5H-indolo[2,3-a]pyrrolo[3,4-c]-carbazole;

12-(3-dimethylaminopropyl)-6,7,12,13-tetrahydro-3(9)-hydroxy-9(3)-methoxy-5,7-dioxo-5H-indolo[2,3-a]pyrrolo[3,4-c]-carbazole;

6,7,12,13-tetrahydro-3,9-dihydroxy-5,7-dioxo-5H-indolo[2,3-a]pyrrolo[3,4-c]carbazole;

12-(2-cyanoethyl)-6,7,12,13-tetrahydro-3,9-dihydroxy-13-methyl-5,7-dioxo-5H-indolo[2,3-a]pyrrolo[3,4-c]-carbazole;

13-(3-dimethylaminopropyl)-6,7,12,13-tetrahydro-3-hydroxy-12-methyl-5,7-dioxo-5H-indolo[2,3-a]pyrrolo[3,4-c]carbazole; or 12-(3-diisopropylaminopropyl)-6,7,12,13-tetrahydro-3-hydroxy-13-methyl-5,7-dioxo-5H-indolo[2,3-a]pyrrolo-[3,4-c]-carbazole.

23. The method of claim 1, where the imide is:
12-(3-aminopropyl)-6,7,12,13-tetrahydro-13-methyl-5,7-dioxo-5H-indolo[2,3-a]pyrrolo[3,4-c]carbazole;

13-(3-aminopropyl)-6,7,12,13-tetrahydro-3-methoxy-12-methyl-5,7-dioxo-5H-indolo[2,3-a]pyrrolo[3,4-c]-carbazole;

13-(3-aminopropyl)-3-chloro-6,7,12,13-tetrahydro-9-methoxy-12-methyl-5,7-dioxo-5H-indolo[2,3-a]pyrrolo[3,4-c]carbazole or 13-(3-isopropylaminopropyl)-6,7,12,13-tetrahydro-13-methyl-5,7-dioxo-5H-indolo[2,3-a]pyrrolo[3,4-c]-carbazole.

24. The method of claim 1 wherein the imide is:
12-(2-Carbamoylethyl)-6,7,12,13-tetrahydro-5,7-dioxo-5H-indolo[2,3-a]pyrrolo[3,4-c]carbazole.

25. The method of claim 1 wherein the imide is:
(±)-12-(3-Diethylamino-2-hydroxy-1-propyl)-6,7,12,13-tetrahydro-5,7-dioxo-5H-indolo[2,3-a]pyrrolo-[3,4-c]carbazole.

26. The method of claim 1 wherein the imide is:
12-(3-dimethylaminopropyl)-6,7,12,13-tetrahydro-3,9-dimethoxy-5,7-dioxo-5H-indolo[2,3-a]pyrrolo[3,4-c]-carbazole;

6,7,12,13-tetrahydro-3,9-dimethoxy-12-methyl-5,7-dioxo-5H-indolo[2,3-a]pyrrolo[3,4-c]carbazole;

6,7,12,13-tetrahydro-12-methyl-5,7-dioxo-5H-indolo-[2,3-a]pyrrolo[3,4-c]carbazole;

6,7,12,13-tetrahydro-3-methoxy-12-methyl-5,7-dioxo-5H-indolo[2,3-a]pyrrolo[3,4-c]carbazole;

6,7,12,13-tetrahydro-12,13-dimethyl-5,7-dioxo-5H-indolo[3,4-a]pyrrolo[3,4-c]carbazole;

6,7,12,13-tetrahydro-12,13-diethyl-5,7-dioxo-5H-indolo[2,3-a]pyrrolo[3,4-c]carbazole; or 6,7,12,13-tetrahydro-5,7-dioxo-3,9-di-n-propoxy-5H-indolo[2,3-a]pyrrolo[3,4-c]carbazole.

27. The method of claim 1, wherein the imide is:
12-(2,3-Dihydroxy-1-propyl)-6,7,12,13-tetrahydro-5,7-dioxo-5H-indolo[2,3-a]pyrrolo[3,4-c]carbazole.

28. The method of claim 1, wherein the imide is:
12-(4-aminobutyl)-6,7,12,13-tetrahydro-13-methyl-5,7-dioxo-5H-indolo[2,3-a]pyrrolo[3,4-c]carbazole or 12-(5-aminopentyl)-6,7,12,13-tetrahydro-13-methyl-5,7-dioxo-5H-indolo[2,3-a]pyrrolo[3,4-c]carbazole.

29. A method of inhibiting myosin light chain kinase in a mammal in need thereof comprising administering to the mammal an effective amount of an indolocarbazole imide of the general formula (I)

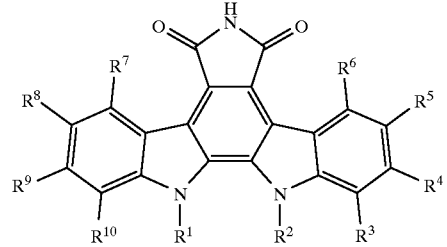

FORMULA I in which $R^1$ and $R^2$ are the same or different and, in each case, is a hydrogen atom or a methyl, ethyl, cyanomethyl, 2-cyano-ethyl, 3-cyanopropyl, 3-cyano-2-propyl, 2-azidoethyl, 3-azido-propyl, 2,3-dihydroxypropyl, 3-chloro-2-hydroxy-1-propyl, 3-amino-propyl, 3-dimethylaminopropyl, 3-trimethylammoniopropyl, 4-aminobutyl, 5-aminopentyl, 3poxymethyl, 3-methylaminopropyl, 3-ethylaminopropyl, 3-isopropylaminopropyl, 3-diisopropylamino-propyl, 3-methylamino-2-ydroxy-1-propyl, 3-ethylaminol-2-hydroxy-1-propyl, 3-isopropylamino-2-hydroxy-1-propyl, 3-dimethylamino-2-hydroxy-1-propyl, 3-diethylamino-2-hydroxy-1-propyl, 3 -diisopropylamino-2-hydroxy-1-propyl, 3-pyrrolidino-2-hydroxy-1-propyl or the radical —(CH$_2$)$_2$CONH$_2$;

$R^3$ and $R^{10}$, independently of one another, each stand for hydrogen, methyl, methoxy, n-propoxy, chlorine, bromine, nitro, hydroxyl or amino or two neighboring radicals together stand for a methylenedioxy radical, in each case with the proviso that if $R^3$ and $R^{10}$ simultaneously stand for hydroxyl groups, not all of the symbols $R^1$ to $R^{10}$ stand for hydrogen atoms, or the pharmacologically acceptable salt thereof.

30. A method of inhibiting myosin light chain kinase in a mammal in need thereof comprising administering to the mammal an effective amount of an indolocarbazole imide selected from the group consisting of:

(±)-12-(3-dimethylamino-2-hydroxy-1-propyl)-6,7,12,13-tetrahydro-13-methyl-5,7-dioxo-5H-indolo[2,3-a]pyrrolo-[3,4-c]carbazole;

(±)-12-(3-diethylamino-2-hydroxy-1-propyl)-6,7,12,13-tetrahydro-13-methyl-5,7-dioxo-5H-indolo[2,3-a]pyrrolo-[3,4-c]carbazole;

(±)-13-(3-dimethylamino-2-hydroxy-1-propyl)-6,7,12,13-tetrahydro-3-methoxy-12-methyl-5,7-dioxo-5H-indolo-[2,3-a]pyrrolo[3,4-c]carbazole;

(±)-12-(3-dimethylamino-2-hydroxy-1-propyl)-6,7,12,13-tetrahydro-3-methoxy-13-methyl-5,7-dioxo-5H-indolo-[2,3-a]pyrrolo[3,4-c]carbazole;

(±)-12-(3-diisopropylamino-2-hydroxy-1-propyl)-6,7,12,13-tetrahydro-13-methyl-5,7-dioxo-5H-indolo[2,3-a]pyrrolo-[3,4-c]carbazole;

(±)-12-(3-pyrrolidino-2-hydroxy-1-propyl)-6,7,12,13-tetrahydro-13-methyl-5,7-dioxo-5H-indolo[2,3-a]pyrrolo-[3,4-c]carbazole and 12-[3-(4-methylphenylsulphonyloxy)-propyl]-6,7,12,13-tetrahydro-13-methyl-5,7-dioxo-5H-indolo[2,3-a]-pyrrolo[3,4-c]carbazole.

* * * * *

UNITED STATES PATENT AND TRADEMARK OFFICE
CERTIFICATE OF CORRECTION

PATENT NO. : 5,945,440
DATED : Aug. 31, 1999
INVENTOR(S) : Kleinschroth et al.

It is certified that error appears in the above-identified patent and that said Letters Patent is hereby corrected as shown below:

Column 32, line 46, remove "3" insert -- e --.

Column 32, line 49, remove "3-ethylaminol" insert -- 3-ethlamino --.

Signed and Sealed this

Twenty-ninth Day of August, 2000

Attest:

Q. TODD DICKINSON

*Attesting Officer*  *Director of Patents and Trademarks*